US012186074B2

(12) United States Patent
Moffat et al.

(10) Patent No.: US 12,186,074 B2
(45) Date of Patent: Jan. 7, 2025

(54) WEARABLE COMPUTING APPARATUS WITH MOVEMENT SENSORS AND METHODS THEREFOR

(71) Applicant: INTERAXON INC, Toronto (CA)

(72) Inventors: Graeme Daniel Moffat, Toronto (CA); Christopher Allen Aimone, Toronto (CA); Hubert Jacob Banville, Toronto (CA); Nicole Hélène Proulx, Hearst (CA)

(73) Assignee: INTERAXON INC., Toronto (CA)

( * ) Notice: Subject to any disclaimer, the term of this patent is extended or adjusted under 35 U.S.C. 154(b) by 293 days.

(21) Appl. No.: 16/959,833

(22) PCT Filed: Jan. 4, 2019

(86) PCT No.: PCT/CA2019/050008
§ 371 (c)(1),
(2) Date: Jul. 2, 2020

(87) PCT Pub. No.: WO2019/134043
PCT Pub. Date: Jul. 11, 2019

(65) Prior Publication Data
US 2020/0367789 A1 Nov. 26, 2020

Related U.S. Application Data

(60) Provisional application No. 62/613,891, filed on Jan. 5, 2018.

(51) Int. Cl.
*A61B 5/11* (2006.01)
*A61B 3/113* (2006.01)
(Continued)

(52) U.S. Cl.
CPC .............. *A61B 5/1116* (2013.01); *A61B 3/113* (2013.01); *A61B 5/1114* (2013.01);
(Continued)

(58) Field of Classification Search
CPC ........ A61B 2505/09; A61B 2562/0204; A61B 2562/0219; A61B 3/113; A61B 5/0022;
(Continued)

(56) References Cited

U.S. PATENT DOCUMENTS 9,517,008 B1 * 12/2016 Berme ................ A61B 5/4023
2009/0239710 A1 * 9/2009 Shemesh .............. A61B 5/1124
482/8

(Continued)

FOREIGN PATENT DOCUMENTS

WO 2015164944 A1 11/2015

OTHER PUBLICATIONS

WIPO, International Search Report and Written Opinion for PCT Application No. PCT/CA2019/050008 dated Apr. 10, 2020.
(Continued)

*Primary Examiner* — Alex M Valvis
*Assistant Examiner* — Nidhi N Patel
(74) *Attorney, Agent, or Firm* — Norton Rose Fulbright Canada LLP

(57) ABSTRACT

There is provided a wearable system for determining at least one movement property. The wearable system includes a head-mounted device including at least one movement sensor; a processor connected to the head-mounted device; and a display connected to the processor. The processor includes a medium having instructions stored thereon that when executed cause the processor to: obtain sensor data from the at least one movement sensor; determine at least one movement property based on the obtained sensor data; and display the at least one movement property on the display. There is also provided a method for displaying the at least one movement property.

18 Claims, 13 Drawing Sheets

(51) Int. Cl.
*A61B 5/00* (2006.01)
*A61B 5/374* (2021.01)
*A61B 5/377* (2021.01)
*A63B 71/06* (2006.01)

(52) U.S. Cl.
CPC ............ *A61B 5/1118* (2013.01); *A61B 5/374* (2021.01); *A61B 5/377* (2021.01); *A61B 5/6803* (2013.01); *A61B 5/6814* (2013.01); *A63B 71/06* (2013.01); *A63B 2071/0694* (2013.01)

(58) Field of Classification Search
CPC ..... A61B 5/0077; A61B 5/024; A61B 5/1114; A61B 5/1116; A61B 5/1118; A61B 5/14542; A61B 5/1495; A61B 5/165; A61B 5/369; A61B 5/374; A61B 5/377; A61B 5/398; A61B 5/486; A61B 5/6803; A61B 5/6814; A61B 5/6824; A61B 5/6828; A61B 5/6829; A61B 5/6831; A61B 5/6895; A61B 7/00; A61B 5/7257; A61B 5/7275; A61B 5/7455; A63B 2071/0694; A63B 71/06; G16H 40/67; G16H 50/30
See application file for complete search history.

(56) References Cited

U.S. PATENT DOCUMENTS

| | | | |
|---|---|---|---|
| 2011/0098608 A1* | 4/2011 | Griffiths | A61B 5/7214 600/595 |
| 2016/0029943 A1* | 2/2016 | Mizuochi | A61B 5/0022 600/595 |
| 2017/0046979 A1* | 2/2017 | Lehary | A63B 69/00 |
| 2017/0188895 A1* | 7/2017 | Nathan | A61B 5/1118 |
| 2020/0122746 A1* | 4/2020 | Sugiura | B60W 60/0053 |

OTHER PUBLICATIONS

Maruta, J. et al.: "Dynamic visuomotor synchronization: Quantification of predictive timing", Sep. 7, 2012 (Jul. 9, 2012), DOI: 10.3428/s13428-012-0248-3—Behavior Research Methods 45(1).

* cited by examiner

WEARABLE COMPUTING APPARATUS WITH MOVEMENT SENSORS AND METHODS THEREFOR

CROSS-REFERENCE TO RELATED APPLICATIONS

This application claims priority from U.S. Provisional Patent Application No. 62/613,891 filed on Jan. 5, 2018, the entire contents of which are hereby incorporated by reference herein.

FIELD

The present relates to wearable devices, and more particularly, to wearable devices with movement sensors.

BACKGROUND

A user may interact with a computing device for example using a keyboard, mouse, track pad, touch screen, or motion-capture devices. As the ways in which humans interact with computing devices change, computers may become usable for new purposes, or more efficient in performing existing tasks. A user command to a computing device that may require several commands on a keyboard may be instead associated with a single hand gesture captured and processed by a motion-capture input device. As the human body has many parts which may be controlled through voluntary movement, there are opportunities for capturing and interpreting other movements for interacting with a computing device.

Bio-signals are signals that are generated by biological beings that can be measured and monitored. Electroencephalographs, galvanometers, and electrocardiographs are examples of devices that are used to measure and monitor bio-signals generated by humans.

A human brain generates bio-signals such as electrical patterns known, which may be measured/monitored using an electroencephalogram ("EEG"). These electrical patterns, or brainwaves, are measurable by devices such as and EEG. Typically, an EEG will measure brainwaves in an analog form. Then, these brainwaves may be analyzed either in their original analog form or in a digital form after an analog to digital conversion.

Measuring and analyzing bio-signals such as brainwave patterns can have a variety of practical applications. For example, brain computer interfaces ("BCI") have been developed that allow users to control devices and computers using brainwave signals.

SUMMARY

In accordance with an aspect of the embodiments described herein, there is provided a wearable system for determining at least one movement property. The wearable system includes a head-mounted device including at least one movement sensor; a processor connected to the head-mounted device; and a display connected to the processor. The processor includes a medium having instructions stored data that when executed cause the processor to: obtain sensor data from the at least one movement sensor; determine at least one movement property based on the obtained sensor data; and display the at least one movement property on the display.

According to an aspect, there is provided a wearable system for determining at least one movement property comprising: a head-mountable device including at least one movement sensor, for sensing a head of a user; a processor in communication with the at least one movement sensor; and a display in communication with the processor; a memory in communication with said processor, said memory storing instructions thereon that when executed cause the processor to: obtain sensor data from the at least one movement sensor; determine at least one movement property relating to movement of a body part of the user based at least in part on the sensor data; and display the at least one movement property on the display.

In some embodiments, the memory stores instructions thereon that when executed cause the processor to: generate feedback for a user relating to the at least one movement property, the feedback being at least one of visual, auditory and tactile.

In some embodiments, the feedback is provided to the user in real-time.

In some embodiments, the memory stores instructions thereon that when executed cause the processor to: calibrate the sensor data to a frame of reference; determine a target metric within the frame of reference; compare the at least one movement property to the reference metric; and display a representation of the comparison on the display.

In some embodiments, parameters of the frame of reference are determined on the basis of at least one of previous data for a user, a population norm, and an external reference.

In some embodiments, the representation of the comparison is offset by a predetermined value.

In some embodiments, the at least one movement sensor comprises a gyroscope, an accelerometer, a magnetometer, a camera or combination thereof.

In some embodiments, the determining of the at least one movement property comprises obtaining a pitch, a yaw, a roll, or combination thereof based on the sensor data obtained from the at least one sensor using an attitude and height reference system algorithm.

In some embodiments, the body part of the user is a body part other than a head of the user.

In some embodiments, the body part of the user is at least one of a torso, a neck, and a limb of the user.

In some embodiments, the at least one movement property comprises a posture metric.

In some embodiments, the at least one sensor comprises a gyroscope and the determination of the posture metric includes determining at least one of a pitch and a position, based on the sensor data.

In some embodiments, the memory stores instructions thereon that when executed cause the processor to: display an indicia of the posture metric on the display.

In some embodiments, the indicia of the posture metric comprises a posture indicator including: a posture scale indicating a possible range of posture values; and a posture marker indicating the user's current posture relative to the posture scale.

In some embodiments, a color of the posture scale, the posture marker, or both are modified according to the posture metric.

In some embodiments, the indicia of the posture metric comprises a stylized portion for showing the posture metric.

In some embodiments, the indicia of the posture metric comprises: a reference frame for showing a range of possible positions and a current position indicator overlaid on top of the reference frame for displaying a current position of the user.

In some embodiments, the indicia of the posture metric comprises a desired position indicator showing a desired range of positions for a pose of the user.

In some embodiments, the indicia of the posture metric comprises a previous position range indicator.

In some embodiments, the at least one movement property comprises a cadence metric, wherein the cadence metric is determined based on a periodic movement of the user along at least one axis of rotation chosen from the pitch, the yaw, the roll, or a combination thereof.

In some embodiments, the memory stores instructions thereon that when executed cause the processor to: display an indicia of the cadence metric on the display.

In some embodiments, the indicia of the cadence metric comprises a numerical indicator showing a frequency of the cadence metric.

In some embodiments, the indicia of the cadence metric comprises a stylized portion modified according to a first derivative of the frequency of the cadence metric.

In some embodiments, a color of at least a portion of the indicia of the cadence metric is modified according to a frequency of the cadence metric.

In some embodiments, the at least one movement property comprises a kinematic score.

In some embodiments, the memory stores instructions thereon that when executed cause the processor to: display an indicia of the kinematic score on the display.

In some embodiments, the indicia of the kinematic score comprises: a scale indicator including a time axis and a kinematic score axis; and a kinematic score indicator showing the user's kinematic score on the scale indicator.

In some embodiments, the kinematic score indicator comprises a current score indicator for showing the user's current kinematic score on the scale indicator; and a historical score indicator showing the user's previous kinematic scores on the scale indicator.

In some embodiments, the at least one movement property comprises a stillness metric, and wherein the memory stores instructions thereon that when executed cause the processor to: display an indicia of the stillness metric on the display.

In some embodiments, the indicia of the stillness metric comprises at least one movement indicator, each indicating movements having a frequency within a respective movement frequency range.

In some embodiments, the at least one movement indicator comprises three movement indicators, the three movement indicators being a low frequency movement range, a medium frequency movement range, and a high frequency movement range.

In some embodiments, the low frequency movement range has a frequency of less than about 2 Hz.

In some embodiments, the medium frequency movement range has a frequency of between about 2 Hz and about 5 Hz.

In some embodiments, the high frequency movement range has a frequency of greater than about 5 Hz.

In some embodiments, in a still state, the three movement indicators converge on a focus position, wherein when the three movement indicators are converged.

In some embodiments, the at least one sensor comprises at least one electrophysiological sensor, wherein the movement property comprises a focus metric, and wherein the focus metric is determined based on a brain state, an eye movement, or both.

In some embodiments, the memory stores instructions thereon that when executed cause the processor to: display an indicia of the focus metric on the display.

In some embodiments, the indicia of the focus metric comprises: a scale indicator including a time axis and a focus score axis; and a focus score indicator showing a user's focus score on the scale indicator.

In some embodiments, the focus score indicator comprises a current score indicator for showing the user's current focus score on the scale indicator; and a historical score indicator showing the user's previous focus scores on the scale indicator.

In this respect, before explaining any embodiment described herein in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

Embodiments will now be described, by way of example only, with reference to the attached figures, wherein.

Figure 1:
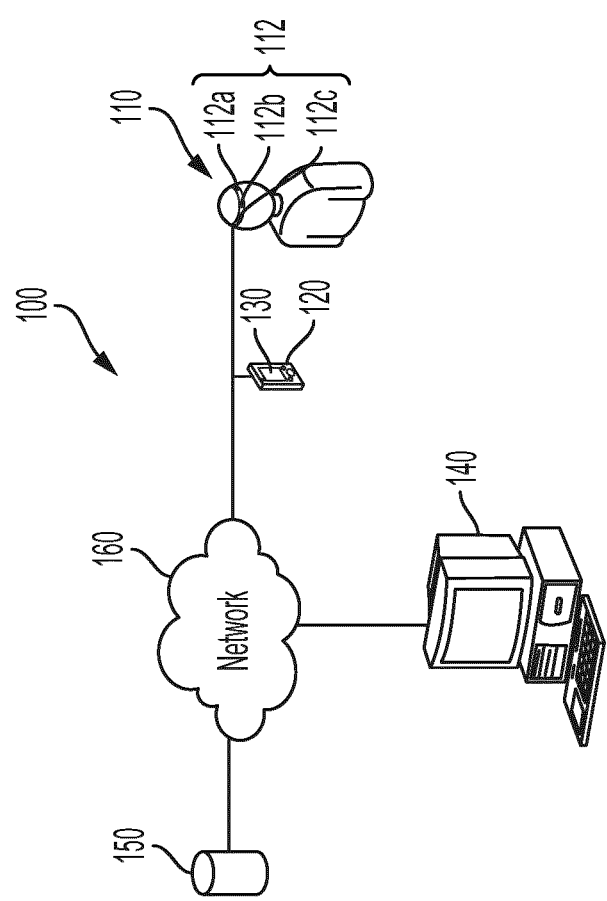
FIG. 1 illustrates a schematic view of an embodiment of a wearable system, according to an embodiment.

In the drawings, the illustrated embodiments are provided by way of example. It is to be expressly understood that the description and drawings are only for the purpose of illustration and as an aid to understanding, and are not intended as a definition of the limits of the invention.

DETAILED DESCRIPTION

As used herein, the term "between" is to be viewed as being an inclusive range unless otherwise indicated. The two endpoints of the range are therefore considered included to be in any recited range.

As used herein, the term "about" preceding a recited value is to be viewed as the recited value including a tolerance range. In some embodiments, "about" means a 10% tolerance from a recited value. For example, in some embodiments, a frequency of about 5 Hz has a lower bound of 4.5 Hz and an upper bound of 5.5 Hz.

A computer system is provided that is implemented by one or more computing devices. The computing devices may include one or more client or server computers in communication with one another over a near-field, local, wireless, wired, or wide-area computer network, such as the Internet, and at least one of the computers is configured to receive signals from sensors worn by a user. In an implementation, the sensors include one more sensors. In some embodiments, the one or more sensors include bio-signal sensors, such as electroencephalogram (EEG) sensors, galvanometer sensors, electrocardiograph sensors, heart rate sensors, eye-tracking sensors, blood pressure sensors, pedometers, gyroscopes, accelerometer, magnetometer, and any other type of sensor. The sensors may be of various types, including: electrical bio-signal sensor in electrical contact with the user's skin; capacitive bio-signal sensor in capacitive contact with the user's skin; blood flow sensor measuring properties of the user's blood flow; and wireless communication sensor placed sub-dermally underneath the user's skin. Other sensor types may be possible. The sensors may be connected to a wearable computing device, such as a wearable headset or headband computer worn by the user. The sensors may be connected to the headset by wires or wirelessly. The headset may further be in communication with another computing device, such as a laptop, tablet, or mobile phone such that data sensed by the headset through the sensors may be communicated to the other computing device for processing at the computing device, or at one or more computer servers, or as input to the other computing device or to another computing device. The one or more computer servers may include local, remote, cloud based or software as a service platform (SAAS) servers. Embodiments of the system may provide for the collection, analysis, and association of particular bio-signal and non-bio-signal data with specific mental states for both individual users and user groups. The collected data, analyzed data or functionality of the systems and methods may be shared with others, such as third party applications and other users. Connections between any of the computing devices, internal sensors (contained within the wearable computing device), external sensors (contained outside the wearable computing device), user effectors, and any servers may be encrypted. Collected and analyzed data may be used to build a user profile that is specific to a user. The user profile data may be analyzed, such as by machine learning algorithms, either individually or in the aggregate to function as a BCI, or to improve the algorithms used in the analysis. Optionally, the data, analyzed results, and functionality associated with the system can be shared with third party applications and other organizations through an API. One or more user effectors may also be provided at the wearable computing device or other local computing device for providing feedback to the user, for example, to vibrate or provide some audio or visual indication to assist the user in achieving a particular mental state, such as a meditative state.

The wearable computing device may include a camera, a display, and bio-signal measuring means to sample a user's environment as well as the user's bio-signals, determining the user's state and context through sensors and user input. The wearable computing device may include at least one user-facing camera to track eye movement. In a particular aspect of the embodiments described herein, the wearable computing device may be in a form resembling eyeglasses wearable on the user's face. Optionally, at least one camera may be oriented to generally align with the user's field of view.

In another aspect of the embodiments described herein, the wearable computing device may be in a form of at least one sensor adapted to being placed at or adhered to the user's head or face. Each sensor may optionally communicate with one another either through wires or wirelessly. Each sensor may optionally communicate with a controller device either through wires or wirelessly. The controller device may be mounted to the wearable computing device in order to reside at or near the user's head or face. Alternatively, the controller device may be located elsewhere on the user's body, such as in a bag or pocket of the user's clothing. The controller device may also be disposed somewhere outside the user's body. For example, the sensors may monitor the user, storing data in local storage mounted to the wearable computing device, and once moving into proximity with the controller device, the sensors, or a transmitter of the wearable computing device may transmit stored data to the controller device for processing. In this implementation, the wearable computing device would be predominantly usable by the user when located nearby the controller device.

The wearable computing device may include a camera, a display and bio-signal measuring means. At least one of the bio-signal measuring means may employ at least one sensor in order to measure brain activity. Brain activity may be measured through electroencephalography ("EEG") techniques electrically, or through functional near-infrared spectroscopy ("fNIR") techniques measuring relative changes in hemoglobin concentration through the use of near infrared light attenuation. A sensor employing pulse oximetry techniques may also be employed in the wearable computing device. Optionally, the wearable computing device may include at least one sensor measuring eye activity using electrooculography ("EOG") techniques. Other sensors tracking other types of eye movement may also be employed.

In various implementations, the wearable computing device may include a variety of other sensors and input means. For example, the wearable computing device may comprise at least one audio transducer such as a single microphone, a microphone array, a speaker, and headphones. The wearable computing device may comprise at least one inertial sensor for measuring movement of the wearable computing device. The wearable computing device may comprise at least one touch sensor for receiving touch input from the user.

The wearable computing device may sample from both the user's environment and bio-signals simultaneously or generally contemporaneously to produce sampled data. The sampled data may be analyzed by the wearable computing device in real-time or at a future predetermined time when not being worn by the user.

The wearable computing device may comprise user input detection methods that are adaptive and improve with use over time. Where the user attempts to command the wearable computing device, and the wearable computing device responds in an unexpected way, the user may attempt to correct the previous input by indicating that the wearable computing device response was incorrect, and retrying the initial command again. Over time, the wearable computing device may refine its understanding of particular user inputs that are corrected. Some user inputs may be easier to successfully measure with a high degree of accuracy than others. It may be preferable to assign a high-accuracy input to command the wearable computing device that the previous input was incorrect. For example, tapping the wearable computing device in a particular spot may indicate that the previous input response was incorrect. Explicit training such as with voice recognition may also be used to configure and command the wearable computing device.

In one implementation, the wearable computing device may be in a glasses-like form factor. Glasses, with or without eyeglass elements, may be well-suited on which to mount sensors as glasses may be easily mounted to the user's face, and are easily removed. Glasses may also be relatively stable in position with respect to the user's head when resting on parts of the user's nose and ears. In order to further reduce movement of the glasses, arm-portions of the glasses may grip sides or rear portions of the user's head. Resilient arm-portions may be particularly useful for achieving a suitable gripping strength, thereby minimizing movement of the glasses and any sensors mounted thereupon.

Optionally, the wearable computing device may itself only provide bio-signal sensors and a processor for processing measurements from the sensors. The wearable computing device may communicate these measurements or data derived from processing the measurements to one or more secondary devices, such as a Google Glass-style device. In any of the implementations, embodiments, or applications discussed herein, it should be understood that some actions may be carried out by a plurality of interconnected devices, or just one of the wearable computing devices of the embodiments described herein. For example, the wearable computing device may not include a display. In such an example, the wearable computing device may communicate visual information to the user through the use of a second device, such as a Google Glass-style device, which does include a display.

Sensors usable with the wearable computing device may come in various shapes and be made of various materials. For example, the sensors may be made of a conductive material, including a conductive composite like rubber or conductive metal. The sensors may also be made of metal plated or coated materials such as stainless steel, silver-silver chloride, and other materials.

In addition to or instead of processing bio-signal measurements on the wearable computing device, the wearable computing device may communicate with one or more computing devices in order to distribute, enhance, or offload the processing of the bio-signal measurements taken or received by the wearable computing device. In particular, the one or more computing devices may maintain or have access to one or more databases maintaining bio-signal processing data, instructions, algorithms, associations, or any other information which may be used or leveraged in the processing of the bio-signal measurements obtained by the wearable computing device. The computing devices may include one or more client or server computers in communication with one another over a near-field, local, wireless, wired, or wide-area computer network, such as the Internet, and at least one of the computers may be configured to receive signals from sensors of the wearable computing device.

The wearable computing device may further be in communication with another computing device, such as a laptop, tablet, or mobile phone such that data sensed by the headset through the sensors may be communicated to the other computing device for processing at the computing device, or at one or more computer servers, or as input to the other computing device or to another computing device. The one or more computer servers may include local, remote, cloud based or software as a service platform (SAAS) servers. Embodiments of the system may provide for the collection, analysis, and association of particular bio-signal and non-bio-signal data with specific mental states for both individual users and user groups. The collected data, analyzed data or functionality of the systems and methods may be shared with others, such as third party applications and other users. Connections between any of the computing devices, internal sensors (contained within the wearable computing device), external sensors (contained outside the wearable computing device), user effectors (components used to trigger a user response), and any servers may be encrypted. Collected and analyzed data may be used to build a user profile that is specific to a user. The user profile data may be analyzed, such as by machine learning algorithms, either individually or in the aggregate to function as a BCI, or to improve the algorithms used in the analysis. Optionally, the data, analyzed results, and functionality associated with the system can be shared with third party applications and other organizations through an API. One or more user effectors may also be provided at the wearable computing device or other local computing device for providing feedback to the user, for example, to vibrate or provide some audio or visual indication to assist the user in achieving a particular mental state, such as a meditative state.

A cloud-based implementation for processing and analyzing the sensor data may provide one or more advantages including: openness, flexibility, and extendibility; manageable centrally; reliability; scalability; being optimized for computing resources; having an ability to aggregate information across a number of users; and ability to connect across a number of users and find matching sub-groups of interest. While embodiments and implementations described herein may be discussed in particular non-limiting examples with respect to use of the cloud to implement aspects of the system platform, a local server, a single remote server, a SAAS platform, or any other computing device may be used instead of the cloud.

In one implementation of the system of the embodiments described herein, a Multi-modal EEG Data-Collection and Adaptive Signal Processing System (MED-CASP System) for enabling single or multi-user mobile brainwave applications may be provided for enabling BCI applications. This system platform may be implemented as a hardware and software solution that is comprised of an EEG headset such as the wearable computing device of the embodiments described herein, a client side application and a cloud service component. The client side application may be operating on a mobile or desktop computing device. The system may provide for: estimation of hemispheric asymmetries and thus facilitate measurements of emotional valence (e.g. positive vs. negative emotions); and better signal-t-noise ratio (SNR) for global measurements and thus improved access to high-beta and gamma bands, which may be particularly important for analyzing cognitive tasks such as memory, learning, and perception. It has also been found that gamma bands are an important neural correlate of mediation expertise.

In the same or another non-limiting exemplary implementation, possible MED-CASP system features may include: uploading brainwaves and associated sensor and application state data to the cloud from mobile application; downloading brainwave & associated data from the cloud; real-time brain-state classification to enable BCI in games or other applications; transmitting real-time brain-state data to other users when playing a game to enable multi-user games; sharing brainwave data with other users to enable asynchronous comparisons of results; sharing brainwave data to other organizations or third party applications and systems; and support of cloud based user profiles for storing personal information, settings and pipeline parameters that have been tuned to optimize a specific user's experience. In this way, usage of the system platform can be device independent.

Each time analysis or processing of user bio-signal data (such as brainwave data) is performed, an instance of aspects of the software implementing the analysis functionality of the embodiments described herein may be generated by the wearable computing device, initiated at either the device or the cloud, in order to analyze the user's private bio-signal data using particular analysis or processing parameters applied during the analysis or processing. For simplicity, such an instance may be referred to as an algorithm "pipeline". Each instance of the pipeline may have an associated pipeline identifier ("ID"). Each pipeline may be associated with a particular activity type, user, bio-signal type of a particular user, application, or any other system platform-related data. Each pipeline may maintain particular pipeline parameters determined to analyze the user's bio-signal data in a particular way, consistent either with previous analysis of the particular user's bio-signal data, consistent with previous analysis of one or more other user's bio-signal data, or consistent with updated data at the cloud server derived from new or updated scientific research pertaining to the analysis of bio-signal data. Pipelines and/or pipeline parameters may be saved for future use at the client computing device or at the cloud. When a new pipeline is created for the user, the wearable computing device or the cloud may provide a new algorithm pipeline ID to be associated with the new pipeline at the cloud and at the device.

Each person's brainwaves are different, therefore requiring slightly different tunings for each user. Each person's brain may also learn over time, requiring the system platform to change algorithm parameters over time in order to continue to analyze the person's brainwaves. New parameters may be calculated based on collected data, and may form part of a user's dynamic profile (which may be called bio-signal interaction profile). This profile may be stored in the cloud, allowing each user to maintain a single profile across multiple computing devices. Other features of the same or another non-limiting exemplary implementation may include: improving algorithms through machine learning applied to collected data either on-board the client device or on the server; saving EEG data along with application state to allow a machine learning algorithm to optimize the methods that transform the user's brainwaves into usable control signals; sharing brainwave data with other applications on mobile device through a cloud services web interface; sharing brainwave data with other applications running on client devices or other devices in the trusted network to provide for the user's brainwave data to control or effect other devices; integration of data from other devices and synchronization of events with brainwave data aid in context aware analysis as well as storage and future analysis; performing time locked stimulation and analysis to support stimulus entrainment event-related potential ("ERP") analysis; and data prioritization that maximizes the amount of useful information obtainable from an incomplete data download (i.e. data is transmitted in order of information salience). The core functionality of the MED-CASP system may be wrapped as an externally-usable library and API so that another developer may use the platform's features in the developer's application(s). The library may be a static library and API for Unity3D, iOS, Android, OSX, Windows, or any other operating system platform. The system platform may also be configured to use a pre-compiled algorithm supplied by a third party within the library, including the ability for a third party developer using the library, to use the developer's own algorithms with the library. The system platform may also support headsets from a variety of vendors; personal data security through encryption; and sharing of un-curated data (optionally using time-limited and fidelity limited access) though the sharing of encryption keys.

Optionally, the wearable computing device of the embodiments described herein may be used to implement aspects of the systems and methods described in PCT Patent Application No. PCT/CA2013/000785, filed Sep. 16, 2013, the entirety of which is incorporated by reference herein. Accordingly, the wearable computing device may be used with a computer network implemented system for improving the operation of one or more biofeedback computer systems. The system may include an intelligent bio-signal processing system that is operable to: capture bio-signal data and in addition optionally non-bio-signal data; and analyze the bio-signal data and non-bio-signal data, if any, so as to: extract one or more features related to at least one individual interacting with the biofeedback computer system; classify the individual based on the features by establishing one or more brainwave interaction profiles for the individual for improving the interaction of the individual with the one or more biofeedback computer systems, and initiate the storage of the brain waive interaction profiles to a database; and access one or more machine learning components or processes for further improving the interaction of the individual with the one or more biofeedback computer systems by updating automatically the brainwave interaction profiles based on detecting one or more defined interactions between the individual and the one or more of the biofeedback computer systems.

Optionally, the wearable computing device may be used to implement aspects of the systems and methods described in PCT Patent Application No. PCT/CA2013/001009, filed Dec. 4, 2013, the entirety of which is incorporated by reference herein. Accordingly, the wearable computing device may be used with a computer system or method for modulating content based on a person's brainwave data, obtained by the sensors of the wearable apparatus of the embodiments described herein, including modifying presentation of digital content at at least one computing device. The content may also be modulated based on a set of rules maintained by or accessible to the computer system. The content may also be modulated based on user input, including through receipt of a presentation control command that may be processed by the computer system of the embodiments described herein to modify presentation of content. Content may also be shared with associated brain state information.

Optionally, the wearable computing device may be used to implement aspects of the systems and methods described in PCT Patent Application No. PCT/CA2014/000004, filed Jan. 6, 2014 the entirety of which is incorporated by reference herein. Accordingly, the wearable computing device may be used with a computer system or method for guiding one or more users through a brain state guidance exercise or routine, such as a meditation exercise. The system may execute at least one brain state guidance routine comprising at least one brain state guidance objective; present at least one brain state guidance indication at the at least one computing device for presentation to at least one user, in accordance with the executed at least one brain state guidance routine; receive bio-signal data of the at least one user from the at least one bio-signal sensor, at least one of the at least one bio-signal sensor comprising at least one brainwave sensor, and the received bio-signal data comprising at least brainwave data of the at least one user; measure performance of the at least one user relative to at least one brain state guidance objective corresponding to the at least one brain state guidance routine at least partly by analyzing the received bio-signal data; and update the presented at least one brain state guidance indication based at least partly on the measured performance. The system may recognize, score, and reward states of meditation, thereby optionally gamifying the experience for the user. The system, using bio-signal data measurements measured by the wearable computing device, and in particular brainwave state measurements, may change the state of what is displayed on the display of the wearable computing device. For example, in response to a determination that the user has achieved a particular brain state, or maintained a particular brain state for a period of time, the wearable computing device may update the display to provide an indication of the determination (e.g. indicating to the user what brain state has been achieved, and, optionally for how long) and may further display an indication of a particular reward assigned to the user in response to the determination.

Optionally, the wearable computing device may be used to implement aspects of the systems and methods described in PCT Patent Application No. PCT/CA2014/000256, filed Mar. 17, 2014 the entirety of which is incorporated by reference herein. Accordingly, the wearable computing device may implement a method including: acquiring at least one bio-signal measurement from a user using the at least one bio-signal measuring sensor. The at least one bio-signal measurement may include at least one brainwave state measurement. The wearable computing device may process the at least one bio-signal measurement, including at least the at least one brainwave state measurement, in accordance with a profile associated with the user. The wearable computing device may determine a correspondence between the processed at least one bio-signal measurement and at least one predefined device control action. In accordance with the correspondence determination, the wearable computing device may control operation of at least one component of the wearable computing device. Various types of bio-signals, including brainwaves, may be measured and used to control the device in various ways. The controlling operation of at least one component of the wearable computing device may comprise sharing the processed at least one brainwave state measurement with at least one computing device over a communications network. Thresholds of brain state may be learned from each user.

Optionally, the wearable computing device may be used to implement aspects of the systems and methods described in U.S. Provisional Patent Application No. 62/512,555, filed May 30, 2017 the entirety of which is incorporated by reference herein. Accordingly, the wearable computing device may implement a method including: as part of an interactive VR environment, present content via at least one feedback module, the content including an object in the VR environment; receiving the bio-signal data of the user from a bio-signal sensor, processing the bio-signal data to determine user states of the user, including brain states, the user states processed using a user profile stored in a data storage device accessible by the a processor and the user states including the brain states, and modifying a parameter of the object in the interactive VR environment in response to the user states of the user, wherein the user receives feedback indicating the modification of the object via the at least one feedback module.

In accordance with an aspect of the embodiments described herein, and having reference to FIG. 1, there is provided a wearable system 100 for determining at least one movement property. The system includes a wearable device such as a head-mountable or head-worn device 110. The head-worn device 110 includes at least one movement sensor(s) 112 such as an accelerometer 112a, a gyroscope 112b, a magnetometer 112c, or any combination thereof. In some embodiments, movement sensor(s) 112 include at least one camera (not shown). At least one camera may be a user-facing camera, for example, to track eye movement, or may be oriented to generally align with the user's field of view.

One or more user effectors may also be provided at head-worn device 110 or other local computing device for providing feedback to the user, for example, to vibrate or provide some audio or visual indication to the user. In some embodiments, head-worn device 110 may include a sound generator such as a speaker to provide auditory feedback to a user.

The system 100 also includes a computing device 120 connected to the head-worn device 110 to determine the at least movement property using sensor data from the at least one movement sensor 112. Computing device 120 and/or head-worn device 110 may be connected to a remote computing device 140 and a sensor data store 150 by way of a network 160.

With conventional movement trackers, such as activity or movement trackers, sensors are typically located on a user's limb, such as an arm or leg, particularly at the wrist or ankle. Sensors were placed at these locations are often used as pedometers. This is because when a person is walking or running, a periodic motion about a particular axis is relatively easy to discern. For example, for a sensor located at the wrist, a person would generally be assumed to walk or run with their arms swaying back and forth. The swaying of the arms includes rotation about the elbow and/or the shoulder. Thus, analysis may be simplified by limiting the data analyzed to rotation about an axis formed by the rotation of the user's arm about the elbow and shoulder. Similarly, for a sensor located at the ankle, the movement of the legs includes an axis of rotation caused by movement about the knee and/or hip. However, transient motions in such limbs may introduce significant noise not easily determined by simple pitch analysis. For example, when a person loses their balance, they may extend their arms and create little circles to try to create gyroscopic forces in an effort to try to regain their balance. Further, for certain activities, movement of a limb could be limited. For example, when cycling, there is limited movement at the wrist. Also, even though there is movement at the feet, it may not provide other potentially useful information. Further still, since a limb is on a side of the user, such as the left side, or right side of the user, the placement of a sensor on a limb adds weight to the side on which it is worn. This weight distribution may throw off a user's balance or lead to unsymmetrical performance.

In contrast, movement of the head may exhibit reduced transient effects, and better weight distribution, which can result in better characterization of a person's overall movement. This may partly be because a person's senses are mostly centered about the head (vision via the eyes, smell via the nose, taste via the mouth, sound via the ears, balance via vestibulo-ocular organs, etc). As such, people often try to stabilize their heads during movement. However, since a person's head is not isolated from the rest of the body (e.g. at least some of the user's movement may be transferred to the head), the movements at the head may provide information about the person's movement.

In some embodiments, the computing device 120 is included on the head-worn device 110. In other embodiments, the computing device 120 is discrete from the head-worn device 110. When the computing device 120 is discrete from the head-worn device 110, the computing device 120 is in wired or wireless connection with the head-worn device 110. When the computing device 120 connects to the head-worn device wirelessly, the computing device 120 includes a network controller 230 to control communication components such as a receiver (not shown), and optionally a transmitter (not shown). The head-worn device 110 includes a transmitter 114 configured to transmit a signal, such as the sensor signal, to be received by computing device 120. The head-worn device 110 optionally includes a receiver configured to receive a signal from the transmitter of computing device 120.

In some embodiments, the system 100 includes a display 130, for example as part of computing device 120, for displaying the at least one movement property. In some embodiments, system 100 includes one or more displays 130. In some embodiments, each one of the head-worn device 110, the computing device 120, and a remote computing device 140, may, independently, include a display 130. In some of the embodiments where the head-worn device 110 includes a display 130, the display is part of an augmented reality device, such as an AR or VR device. In some of the embodiments where the computing device 120 includes a display 130, the computing device 120 is a bike-mounted computer or a smart phone. In some embodiments, a remote user (such as a trainer, coach, supporter, or spectator) may view the at least one movement property at the remote computing device 140 including the display 130. In some embodiments, there are multiple remote computing devices 140. In some embodiments, the at least one movement property is displayed on a heads-up display included on the device 110, a vehicle-mounted display (such as on a bike-mounted device), a remote computing device or terminal (such as one used by a coach), or any combination thereof.

In some embodiments, the system 100 includes a sensor data store 150 connected to the device 110 for storing sensor data from the at least one movement sensor 112. The sensor data store 150 may be part of the device 110 or the computing device 120, or is connected to a network 160 accessible by the device 110 or the computing device 120.

Figure 2:
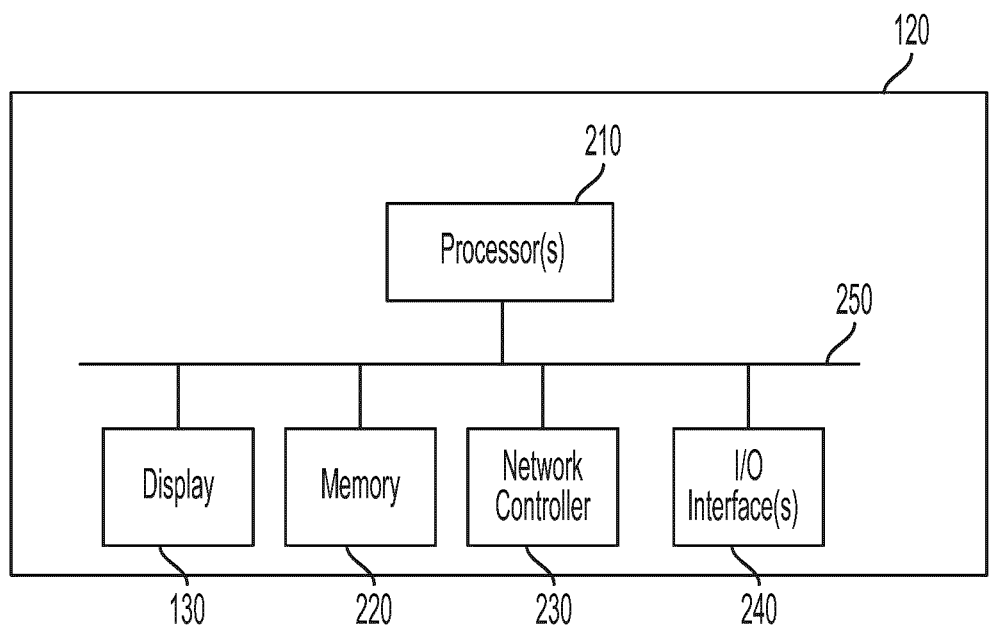
FIG. 2 illustrates is a block diagram of example hardware components of a computing device of the wearable system of FIG. 1, according to an embodiment.

FIG. 2 is a high-level block diagram of computing device 120, for example, a mobile computing device. As will become apparent, computing device 120, under software control, may receive sensor data from movement sensor(s) 112 for processing by one or more processors 210 to analyze the sensor data. Processed sensor data, for example, at least one movement property, may be used for post-activity review.

As illustrated, computing device 120 includes one or more processor(s) 210, display 130, memory 220, a network controller 230, and one or more I/O interfaces 240 in communication over bus 250.

Processor(s) 210 may be one or more Intel x86, Intel x64, AMD x86-64, PowerPC, ARM processors or the like.

Memory 220 may include random-access memory, read-only memory, or persistent storage such as a hard disk, a solid-state drive or the like. Read-only memory or persistent storage is a computer-readable medium. A computer-readable medium may be organized using a file system, controlled and administered by an operating system governing overall operation of the computing device.

Network controller 230 serves as a communication device to interconnect the computing device with one or more computer networks such as, for example, network 160, such as a local area network (LAN) or the Internet, and sensor data store 150 and remote computing device 140.

One or more I/O interfaces 240 may serve to interconnect the computing device 120 with peripheral devices, such as for example, keyboards, mice, video displays, and the like. Such peripheral devices may include a display of device 120. Optionally, network controller 230 may be accessed via the one or more I/O interfaces.

Software instructions are executed by processor(s) 210 from a computer-readable medium. For example, software may be loaded into random-access memory from persistent storage of memory 220 or from one or more devices via I/O interfaces 240 for execution by one or more processor(s) 210. As another example, software may be loaded and executed by one or more processor(s) 210 directly from read-only memory.

In some embodiments, computing device 120 may be an embedded system or microcontroller, including a processor, memory, and input/output (I/O) peripherals on a single integrated circuit or chip, to perform the processes and store the instructions and data described herein. In an example, computing device 120 may be a microcontroller such as an Arduino board and associated software system.

Figure 3:
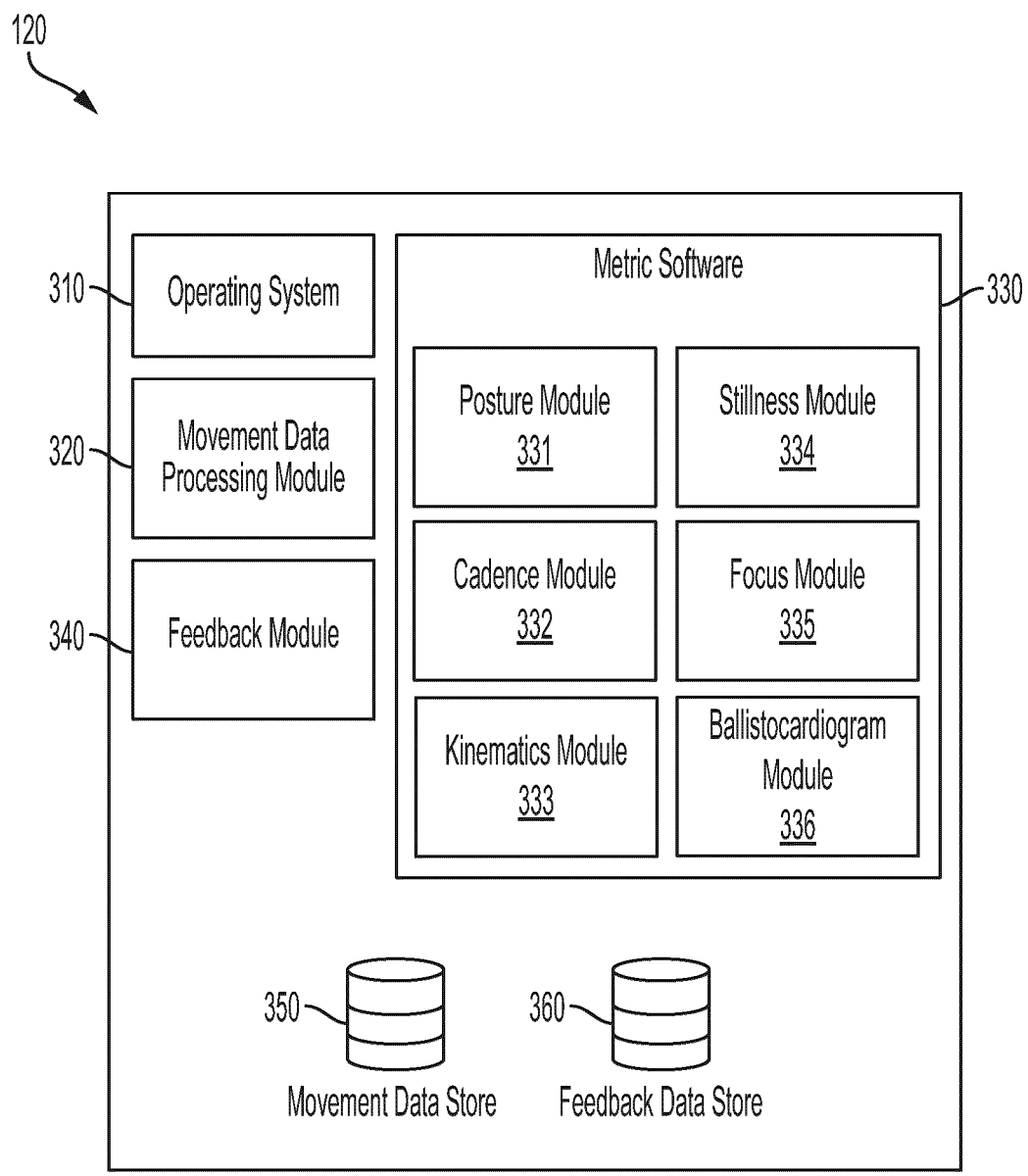
FIG. 3 illustrates the organization of software at the computing device of FIG. 2.

FIG. 3 depicts a simplified organization of example software components and data stored within memory 220 of computing device 120. As illustrated, these software components may include operating system (OS) software 310, movement data processing module 320, metric software 330, feedback module 340, movement data store 350 and feedback data store 360.

Operating system 310 may allow basic communication and application operations related to the computing device. Generally, operating system 310 is responsible for determining the functions and features available at device 120, such as keyboards, touch screen, synchronization with applications, email, text messaging and other communication features as will be envisaged by a person skilled in the art. In an embodiment, operating system 310 may be Android™ operating system software, Linux operating system software, BSD derivative operating system software, iOS™ operating system software, or any other suitable operating system software. In embodiments in which an Android operating system platform is in use, software components described herein may be implemented using features of a framework API (Application Programming Interface) for the Android platform.

Movement data processing module 320 may be configured to adapt processor(s) 210 to receive sensor data from movement sensor(s) 112 of head-worn device 110 for processing.

Movement data processing module 320 may be configured to perform a physical calibration of the electrical output of movement sensor(s) 112 to a physical meaning. For example, there may be an initial calibration of movement sensor(s) when head-worn device 110 is first used to have the user perform specific movements and maintain predefined positions to calibrate the movement sensor(s) 112 to the user's specific body and movement patterns.

Initial calibration may also be performed to address drift or error from movement sensor(s) 112 sensor data. An initial calibration may be performed at the start of each session of use of head-worn device 110.

Movement data processing module 320 may be further configured to calibrate the sensor data from movement sensor(s) 112 to a frame of reference. Calibration may be performed on sensor data, or for metrics determined from sensor data, for example, by metric software 330. In some embodiments, the frame of reference may serve as a reference frame for showing a range of possible positions in feedback on a metric.

In an example, calibration may be performed for sensor data received from movement sensor(s) 112 such as accelerometer 112*a*, gyroscope 112*b*, magnetometer 112*c* in connection with a frame of reference of a camera. For example, a camera may track relative to an object in the world or external environment of the visible frame of reference captured by the camera. Thus, movement of a user's head may be compared to other objects in the world. In this way, movement may be considered relative to a frame of reference provided by the camera, in addition to a gravitational field of reference, for example by way of accelerometer 112*a*.

A camera may also be used in determination of concentration and perception metrics relative to a moving object in a user's environment that the camera detects. A user's movement patterns, as detected by other movement sensor(s) 112 such as accelerometer 112*a*, gyroscope 112*b*, magnetometer 112*c* may be analyzed for patterns related to images of objects that appear in a camera similar to a user's field of vision, for example, to determine if a user performs certain movements or uses up too much energy in reaction to an item in the user's field of vision.

The parameters of a frame of reference may be determined from a number of different calibration modes, for example, from a user's previous sensor data or metrics, target metrics set by a user, population norms for a metric, parameters for sensor data or metrics set by a user's coach or other reference plan.

Such calibration may be used to determine what the upper and lower limits of a sensed movement should be. In some embodiments, such calibration may be used to set a baseline of a particular metric.

The parameters of a frame of reference may also define specific goals or targets, such as target metrics, for a user to achieve, by a particular position or movement of the user's body, detected using movement sensor(s) 112, and the associated determined metric. A target metric may be an absolute or relative value, or may be a range of values. In an example, a calibration may be used to define an ideal state for a user's metric, such as a reference posture. An ideal reference posture may be different for each user.

In some embodiments, a frame of reference for a metric may be defined with reference to norms within a given population of users.

In some embodiments, target metrics may be based on input from a coach or other user or reference.

In some embodiments, target metrics may be developed using machine learning techniques. In an example, machine learning may be used to detect patterns in previous sensor data and/or metric data. In some embodiments, other user data on sensor data and/or metric data may be analyzed to identify user's with similar profiles to the present user, such that appropriate targets may be established.

In another example, a decision tree may be used to classify a user into different types to assign a training strategy for the user, defining a frame of reference for the movement sensor data and target metrics.

In an example, a race strategy may be developed for a user by analysis of previous race sensor data and metric data, in an attempt to model the user's best race, to use as a target.

Movement data processing module 320 may be configured to model optimal efficiency of movement for a user's body, based on measurements received from movement sensor(s) 112, to determine if a user is wasting energy.

Metric software 330 may include one or more submodules for processing sensor data received from movement sensor(s) 112. As illustrated, metric software 330 includes a posture module 331 for determining a posture metric based at least in part on sensor data, a cadence module 332 for determining a cadence metric based at least in part on sensor data, a kinematics module 333 for determining a kinematics metric based at least in part on sensor data, a stillness module 334 for determining a stillness metric based at least in part on sensor data, a focus module 335 for determining a focus metric based at least in part on sensor data, and a ballistocardiogram module 336 for determining a heart rate and heartbeat metric based at least in part on sensor data.

Feedback module 340 may be configured to generate feedback, for example, as visual, auditory or tactile feedback, for presentation to a user based on metrics determined by metric software 330.

Target metrics determined by movement data processing module 320 may also be used to form feedback to a user. In an example, target metrics may be displayed concurrently with near real-time metrics determined by metric software 330, based at least in part on sensor data received from movement sensor(s) 112 in near real-time, and displayed to a user.

Both metrics determined by metric software 330 and the references developed in the movement data processing module 320 may be provided as visual, auditory and/or tactile feedback for presentation to the user. In this way, a user may be able to visualize or receive easy to understand measure of progress towards a target or a goal, while under exertion.

In some embodiments, a sensed metric and/or a target metric may be modified for visual, auditory or tactile feedback to effect a change in a user's performance by introducing an artificial offset or error in the feedback, to encourage particular behaviour in the user. In an example, a user's cadence metric may be presented to the user as lower than the actual determined, so as to encourage the user to increase their effort. This offset, or bias, in feedback may be based on expert input from a coach, or developed using machine learning techniques.

In use, in some embodiments, the computing device 120 determines the at least one movement property using data received from the at least one movement sensor 112 in real-time or near real-time. In some embodiments, the at least one movement property is determined for post-activity review.

Processor(s) 210 of computing device 120 may execute movement data processing module 320 for an initial calibration the first time head-worn device 110 is used, or at the start of a particular session of a user using head-worn device 110 in which sensor data is being obtained from movement sensor(s) 112. Further calibration tasks of movement data processing module 320, for example, defining a frame of reference or establishing a target metric for a user, may be called at any other time during which sensor data is being received from movement sensor(s) 112, for example during method 1400. Both a measured metric from movement sensor(s) 112 and a calibrated reference or target determined at movement data processing module 320 may be displayed together as feedback for a user.

In an example, a user's cadence metric may be compared to a target cadence goal, and presented to a user.

Figure 4:
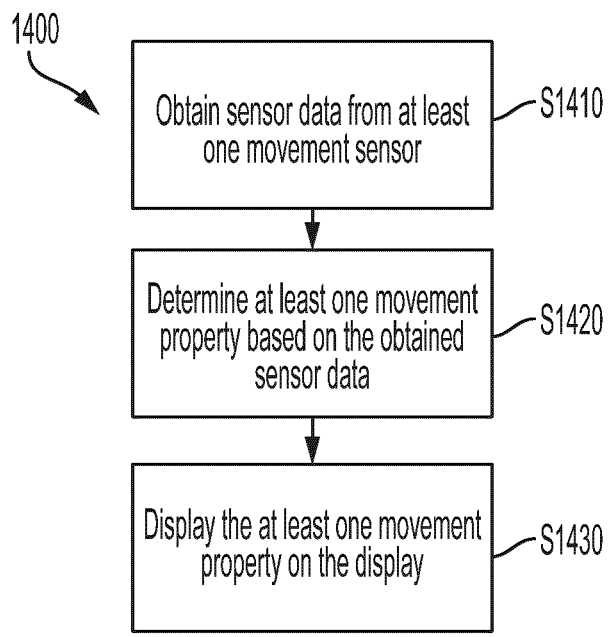
FIG. 4 illustrates a flow chart of a method for determining a movement property, performed by the software of FIG. 3, according an embodiment.

FIG. 4 illustrates a method 1400 for determining at least one movement property from sensor data obtained from at least one movement sensor 112. The steps are provided for illustrative purposes. Variations of the steps, omission or substitution of various steps, or additional steps may be considered. Blocks S1410 is performed by processor(s) 210 executing movement data processing module 320. Block S1420 is performed by processor(s) 210 executing metric software 330. Block S1430 is performed by processor(s) 210 executing feedback module 340.

At block S1410, sensor data is received from at least one movement sensor 112.

At block S1420, metric software 330 processes the sensor data to determine at least one movement property, in an example, one or more metric(s) as described herein.

When the at least one movement property is determined for post-activity review, the computing device 120 optionally analyzes sensor data from the sensor data store 150. This may reduce computational load on the computing device 120 as compared to buffering the sensor data from the at least one movement sensor 112 directly.

In some embodiments, the at least one movement property is determined in real-time, near-real-time, in a post activity period, or combination thereof. In some embodiments, the sensor data is time-stamped. Time-stamped sensor data (or data or scores derived therefrom) may allow for synchronized display of multiple movement properties, for the display of historical sensor data (or data or scores derived therefrom), reduce computational load, or any combination thereof.

At block S1430, feedback module 340 may generate feedback for a user, for example, based on determined metrics described herein, such as metrics of the user using a bicycle, for example posture, cadence and kinematics.

In some embodiments, the at least one movement property is displayed on the display 130 in real-time or near real-time. This may provide a user with feedback while still engaged in the activity, and they are able to adjust their performance based on the feedback.

Such feedback may allow the user to monitor and adapt their movements. In some embodiments, the at least one movement property is displayed on the display 130 after the activity in order to allow the user or others review the performance.

In some embodiments, the display includes an indicia corresponding to each of the at least one movement property being displayed. In some embodiments, the indicia is modified to show a dynamic change of the corresponding movement property. In some embodiments, each indicia includes a description describing what the at least one movement property measures, how the indicia is varied, what a user should strive for to achieve good performance with respect to the corresponding movement property, or a combination thereof.

In an example, a real-time approach may be used. In use while a user is exercising, a user may went to get into a "groove", and want to see energy ramping up. Using, for example, cadence metrics, a feedback trigger may be presented to the user to increase cadence based on an increasing (by volume or tempo) beat of sound. However, if a detected heart rate is increasing too quickly, a feedback could be presented to the user trigger to have them slow down. The target may be from a calibration, or from previous user data.

At least one movement property may be in the form of a metric of a movement or activity performed by a user. For example, such metrics may include measurements of a biking movement or activity such as posture, cadence, and kinematics, metrics during a yoga movement or activity such as stillness, posture, and focus, and other metrics such as heart rate and heartbeat. These metrics, and how they are determined and displayed, will now be described in further detail.

In some embodiments, one or more metrics may be used to determine an efficiency based on another dimension or measurement. For example, work done, represented by a cadence metric, may be compared to energy output based on a user's heart rate. Thus, an efficient cadence for work done per energy output may be determined, and presented as feedback to a user.

Posture Metrics

In some embodiments, the at least one movement property includes posture metrics related to a user's posture. The posture determination may be based on the activity being undertaken.

Posture of a user, including posture of the user's body parts including head, neck, torso, and limbs may be based on at least one of pitch, roll and yaw of a user's head. For example, the pitch of a user's head may make it possible to detect the posture of the user's torso. In some embodiments, a user's posture may be determined based only on detected pitch of a user's head detected by movement sensor(s) 112 head-mounted on the user on a wearable device.

In some embodiments, the posture is based on the pitch of the person's head. For example, the activity may be cycling. In cycling, resistance to movement may include frictional losses (for example, at the tires, wheel, crank, etc), and aerodynamic drag. As the speed of the vehicle increases, aerodynamic drag has larger effects of the resistance to movement. As such, a person may wish to adopt a body position (e.g. a posture) that reduces the aerodynamic drag. The pitch of the head may be indicative of the amount of aerodynamic drag a user experiences. For example, if a person is looking up, they may be exposing more surface area of their body, resulting in more drag. Thus, an idealized posture might have a person looking straight ahead horizontally, or slightly downward.

Pitch data can be obtained by processing the data from the at least one movement sensor 112. In some embodiments, the at least one movement sensor includes a gyroscope, an accelerometer, a magnetometer, or a combination thereof. In some embodiments, the at least one movement sensor 112 includes a gyroscope 112*b*. In some embodiments, the posture is determined using the pitch data. In some embodiments, any axis of orientation may be used depending on the axis of interest. In some embodiments, the determination of the pitch data includes reducing noise, drift, or both. In some embodiments, the at least one movement sensor 112 further includes at least one of an accelerometer 112a and a magnetometer 112c. Accelerometer data and/or the magnetometer data may be combined with the gyroscope data, for example, using an attitude and heading reference system (AHRS) to determine pitch with reduced noise and/or drift compared to using the gyroscope data on its own. In some embodiments, the accelerometer data corrects for gyroscope drift and optional magnetometer data provides additional correction. In some embodiments, the AHRS is determined using the Madgwick AHRS algorithm. In some embodiments, the reducing of noise, drift, or both includes filtering of sensor data, pitch data, or both. In some embodiments, the processor determines posture data using the pitch data. In some embodiments, the posture is the pitch obtained from the AHRS algorithm. In some embodiments, posture may be obtained from one of or any combination of pitch, roll and yaw of user's head.

For a biking application, posture may be represented by the pitch orientation. For other applications, any axis of orientation could be used depending on the axis of interest. For example, posture could be applied to other sport applications, for example, golf or running. Posture may also be applied to a workplace application, i.e. head posture while working at desk, computer screen or other work environments.

Figure 5:
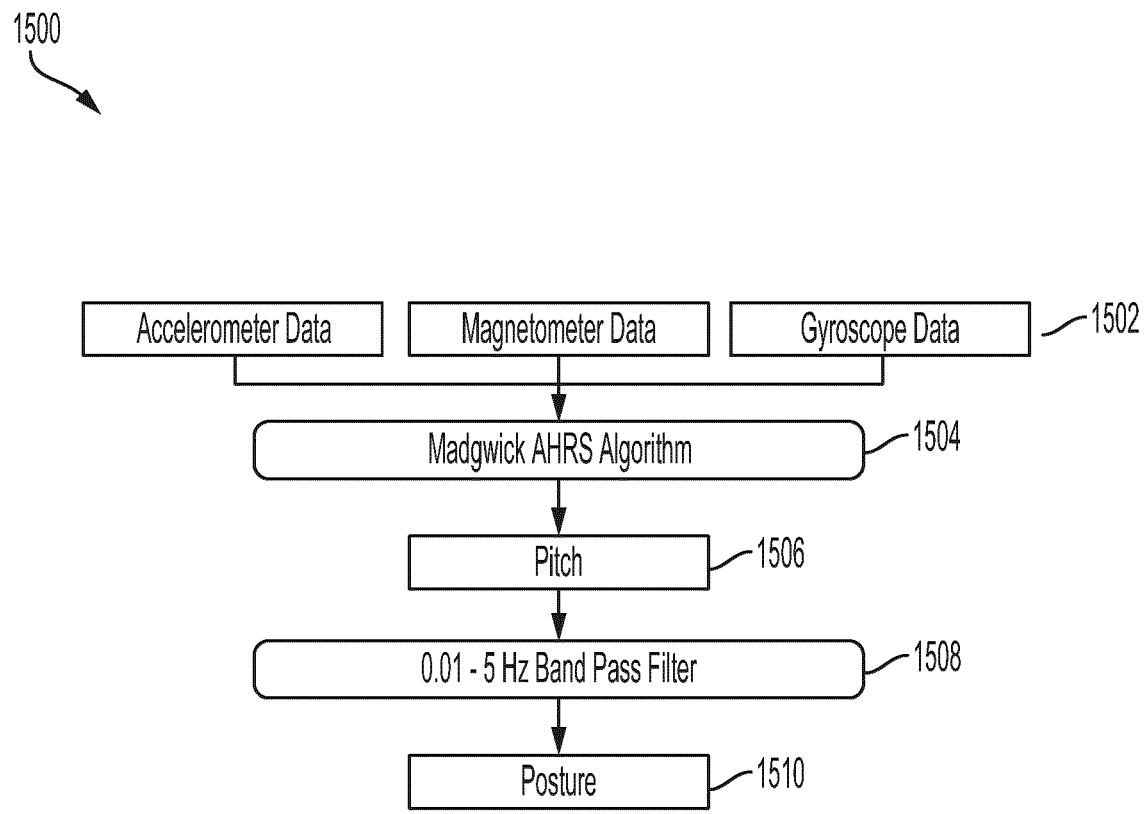
FIG. 5 illustrates a flow chart of a method for determining a posture metric, performed by the software of FIG. 3, according to an embodiment.

FIG. 5 illustrates a flow chart of a method 1500 for determining a posture metric, performed by posture module 331 software of FIG. 3, according to an embodiment. The steps are provided for illustrative purposes. Variations of the steps, omission or substitution of various steps, or additional steps may be considered.

As shown in FIG. 5, sensor data 1502 may be received from movement sensor(s) 112. In particular, accelerometer data may be received from accelerometer 112a, magnetometer data may be received from magnetometer 112c, and gyroscope data may be received from gyroscope 112b.

Sensor data 1502 may then be processed at block 1504 using a Madgwick AHRS algorithm to determine a state of the system, in particular, to determine pitch data 1506.

Pitch data 1506 may then be filtered at block 1508 with a 0.01 to 5 Hz band pass filter to determine posture data 1510.

Figure 11:
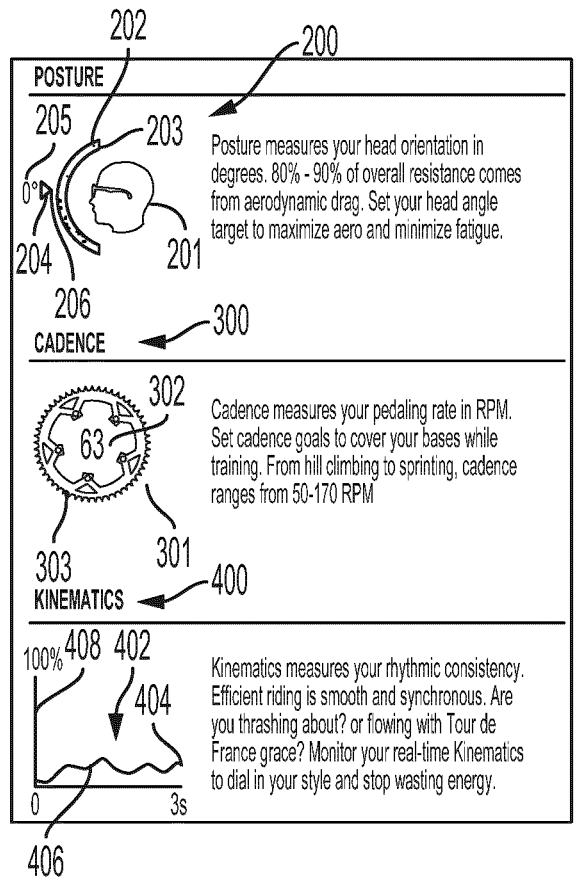
FIG. 11 illustrates movement properties as depicted on a display of an embodiment of a wearable system.

In some embodiments, feedback on a posture metric may be provided to a user in the form of a display. Having reference to FIG. 11, in an embodiment, the display 130 includes an indicia of posture 200.

In some embodiments, the indicia 200 includes a posture indicator 202. In some embodiments, the posture indicator 202 includes a posture scale 203 and a marker 204 next to the posture scale 203. The marker 204 moves relative to the posture scale to indicate the posture of the user. In some embodiments, the indicia includes a numerical posture indicator 205 showing the numerical pitch value of the user.

In some embodiments, the posture scale 203 includes two end points. In some embodiments, the two end points of the posture scale 203 are an upper threshold posture value and a lower threshold posture value. In some embodiments, the upper and lower threshold posture values represent a range of motion, up and down, of the head. For example, the upper threshold posture value may be a pitch of 15°, 30°, 45°, 60°, 75° or even 90°. For example, the lower threshold posture value may be a pitch of −15°, −30°, −45°, −60°, −75°, or even −90°. In some embodiments, the position of the marker 204 relative to the posture scale 203 is varied according to the pitch of the user's head. For example, in some embodiments, when the pitch of the user's head is at an ideal posture position, determined, for example, during calibration, the marker 204 may be located proximate the posture scale 203 at a position between the two endpoints. In some embodiments, the ideal posture position is located at the midpoint of the posture scale 203. As the pitch increases, the marker 204 moves up along the posture scale 203. Conversely, as the pitch decreases, the marker moves down along the posture scale 203. In some embodiments, the posture scale 203 is arcuate. In some embodiments, the midpoint of the arcuate scale 203 is on the same horizontal axis as the origin of the arc. In some embodiments, the arcuate shape is a preferred shape because a user may intuitively understand that the movement is a rotational movement when the posture scale 203 is curved. However, other shapes for the posture scale 203 are also possible, such as a line, an elongate rectangle, or a circular portion.

In some embodiments, the posture indicator 202 includes an ideal posture indicator 205 located proximate to the posture scale 203 to indicate an ideal posture position relative to the posture scale 203. In some embodiments, the ideal posture indicator 205 is located where the marker 204 would be when the user is in the ideal posture. For example, in some embodiments, the ideal posture position is a pitch of 0° and the ideal posture indicator 205 indicates where the marker 204 would be when the user's posture is equal to the ideal posture position. In some embodiments, the ideal posture indicator 206 and the marker 204 are complementary. For example, in some embodiments, the ideal posture indicator 206 is an unfilled outline that is approximately the same size as the marker 204, which is a filled shape.

In some embodiments, the posture scale 203 includes one or more posture range portions to indicate a deviation from a predetermined position, such as an ideal posture position. For example, the one or more posture range portions may include an ideal posture range portion, a tolerable range portion, and an undesired range portion. In some embodiments, these portions are colored, for example, in green, yellow, and red, respectively. For example, in some embodiments, the portions are divided based on the angle of the pitch. In some embodiments, the ideal posture range has an angle, $\alpha$, of $|\alpha|<15°$, the tolerable range portion has an angle, $\beta$, of $15°\leq|\beta|<30°$, and the undesired range portion has an angle, $\gamma$, of $|\gamma|30°$. In these embodiments, as the position of the marker 204 moves relative to the posture scale 203 to indicate the user's portion, the marker 204 would be moved proximate to a posture range portion corresponding to the deviation from ideality.

In some embodiments, the color of the marker 204, the posture scale 203, or both change according to the deviation from the ideal posture position. For example, in some embodiments, the marker 204 is shown in green when the posture of the user is an ideal posture position. The color of the marker 204 may transition from green to yellow as the user's position transitions from the ideal posture position to a tolerable posture position. Similarly, the color of the marker 204 may transition from yellow to red as the user's position transitions from the tolerable posture position to an undesirable posture position.

In some embodiments, the indicia 200 includes a stylized portion 201. In some embodiments, the stylized portion is 201 a representation of a head 201. The representation of the head may be shown, for example, as a side, profile view. Other views are possible, such as a front view. In some embodiments, the posture scale 203 is located proximate the head 201. In some embodiments where the posture scale 203 is arcuate, the origin of the arc may be located on or about the head 201.

In some embodiments, the display of the head 201 is altered to indicate the posture of the user. For example, the head 201 may be rotated when shown as a side profile view. For example, when the posture has a pitch of 0°, the head 201 may be oriented in a neutral position such that an axis running from the top of the head down to the neck is vertical. In those embodiments where the head is shown as a side profile view with the eyes on the left side, as the user starts to tilt their head back, the posture changes such that the pitch is increased and the head is rotated clockwise. Similarly, if the user tilts their head down, the head 201 would be rotated counter-clockwise.

In some embodiments, the posture is based on the position of the user's head. For example, the activity may be yoga. In yoga, a user moves from one pose to another. In some embodiments, each pose includes a desired position and a desired orientation, or some combination thereof. When the user gets into a pose, the position of their head may drift as they hold a pose. As such, in some embodiments, the posture includes a range of desired positions, a range of desired orientations, or some combination thereof. These ranges may be in addition to or an alternative to the desired position and/or the desired orientation.

Figure 12:
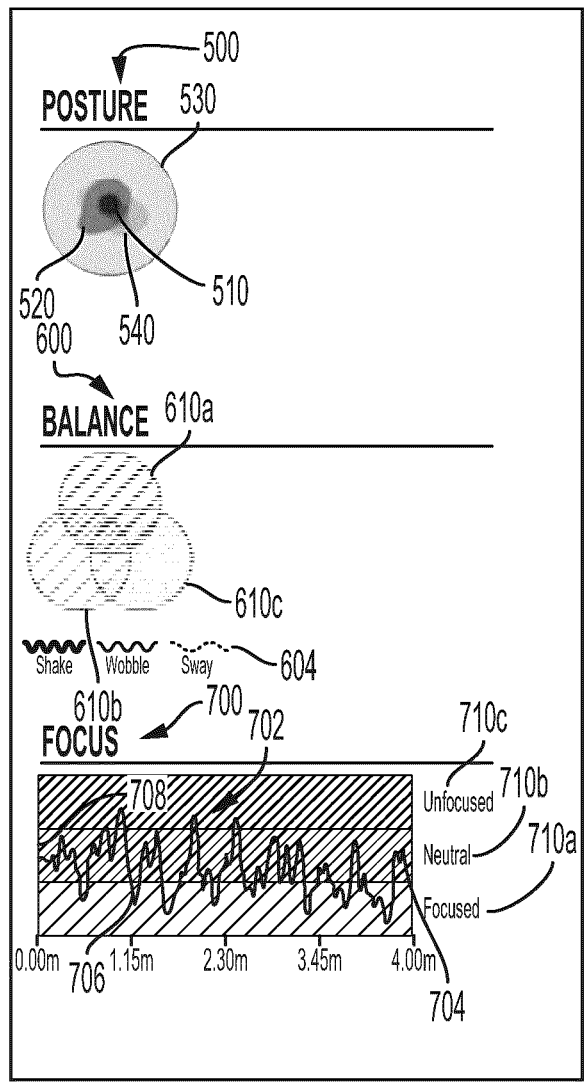
FIG. 12 illustrates movement properties as depicted on a display of an embodiment of a wearable system.

Having reference to FIG. 12, in an embodiment, an indicia of posture 500 is shown. The indicia includes a current position indicator 510. In some embodiments, the current position indicator 510 is a graphical marker, such as a dot. The current position indicator 510 is modified to show the position of the user's head. In some embodiments, the indicia of posture 500 includes a range indicator 530 providing a reference frame, such as a range of possible positions against which the current position indicator 510 moves. Thus, the position indicator 510 moves relative to the range indicator 530 based on the movement of the position of the user's head.

In some embodiments, the display 130 is a 2D display. When the display is a 2D display, the display may not be able to properly represent the position of the head in relation to a 3D space that the user is in. In some embodiments, three axes extend from the user: an x-axis extending to the left and right of the user; a y-axis extending to the front and back of the user; and a z-axis extending above and below the user. Thus, in some embodiments, the position is shown based on the two axes where the majority of a user's motion would be expected for the activity (e.g. during a particular pose for yoga). For example, when standing straight, or in a tree pose, the majority of the movement is expected in the XY-plane, whereas during a side-plank, the majority of the movement is expected in the YZ-plane.

In some embodiments, the indicia of posture 500 includes a desired position range indicator 520. The desired position range indicator 520 shows the desired range of positions that the user position is in during a particular pose. The desired position range indicator 520 may be modified according to a sequence of preprogrammed poses, for example, with a guided meditation. In some embodiments, the desired position range indicator 520 is shown in a first color.

In some embodiments, the indicia of posture 500 includes a previous position range indicator 540. The previous position range indicator 540 shows the range of positions that the user has been in during the pose. In some embodiments, the previous position range indicator 540 is shown in a second color. In some embodiments, the second color is different from the first color. In some embodiments, the previous position range indicator 540 shows previous positions for a time period immediately preceding the user's current position, as shown by current position indicator 510. In some embodiments, the previous position range indicator includes a start time. In some embodiments, the start time is the commencement of a pose in a sequence (e.g. according to time, a guided-session, etc), a transitional time, or a window time. The transitional time is the time to allow the user time to transition from one position to another. In one embodiment, for example, during a guided meditation, the user may be provided with a few seconds after they are instructed to get into a particular pose before position data is shown in the previous position range indicator 540. For example, in some embodiments, the transition time is from about 3 seconds to about 5 seconds. In some embodiments, the transition time is stored in a user preference setting that includes a transition time preference, where the user preference setting is stored on the data store. In another embodiment, the transition time ends after movements of the user are relatively stable. For example, large movements in a user's head position may indicate that the user is getting into the pose. In some embodiments, the transition time is an average movement time between poses. In some embodiments, the window time is a fixed time before the current position. In this manner, the previous position range indicator shows the user's previous position during the window before the current position. Thus, the previous position indicator would be modified to remove position data prior to the window time. In some embodiments, the removal is effected by causing portions of the previous position indicator to disappear or fade.

Figure 13:
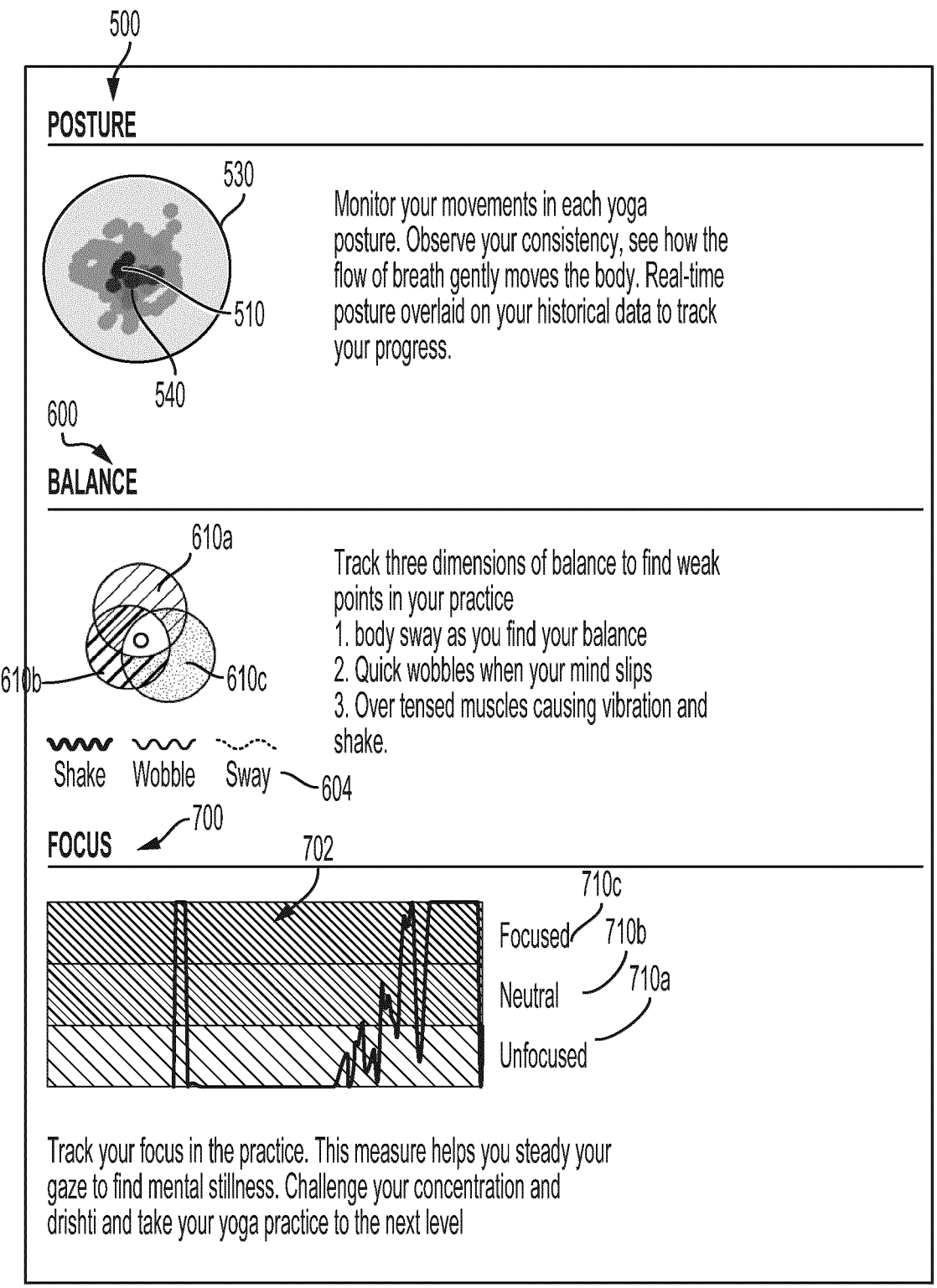
FIG. 13 illustrates movement properties as depicted on a display of an embodiment of a wearable system.

Having reference to FIG. 13, in some embodiments, the previous position range indicator 540 includes a plurality of previous position indicators. The plurality of previous position indicators are spaced a corresponding sequence time apart. In some embodiments, the sequence times are spaced equally. In some embodiments, the previous position indicators fade with more fading corresponding to an earlier previous position. In some embodiments, the previous position range indicator 540 includes a shape showing a range of recent positions.

In some embodiments, the indicia of posture 500 includes an orientation indicator 550. In some embodiments, the orientation indicator 550 is a vector indicating the orientation of the user's head, for example, which way the user is facing.

Cadence Metrics

In some embodiments, the at least one movement property includes cadence metrics. Cadence is a movement property having a cyclic or periodic quality. As such, the cadence includes a frequency. The frequency is a measure of events per unit time. The cadence determination may be based on the activity undertaken. For example, this could be rotations per minute (RPMs) that a cyclist turns their crank, or strokes per minute that a rower rows their boat. In some embodiments, a consistent cadence frequency may be determined to make it possible to predict time of a next event, for example, the next turn of the crank, or at a rotational position, or the next stroke or a rower in their boat.

Where the body's movement has a cyclic or periodic quality, a movement having a corresponding frequency may be detected in the movement of the head. For example, the head may be rotating on one or more axes at the frequency of the cyclic or periodic movement. In some embodiments, the cadence is determined using one axis of rotation. In other embodiments, the cadence is determined using two or more axes of rotation. By using more than one axis of rotation, errors related to non-cyclic movement can be better accounted for. For example, a cyclist may need to turn their head in order to look over their shoulder the location of a peloton or to scan their surroundings to anticipate changes in road conditions or a change in direction.

In some embodiments, the at least one movement sensor 112 includes a gyroscope, accelerometer, magnetometer, or a combination thereof. Cyclic movement data may be determined by processing the data from the at least one movement sensor 112. In some embodiments, the cadence is determined using the cyclic movement data. For example, the cyclic movement data may include a periodic property. In some embodiments, the periodic property includes movement along one or more axes of rotation. The one or more axes of rotation may include a pitch, yaw, roll, or combination thereof. In some embodiments, the frequency of the cadence is a frequency determined from the cyclic movement data. In some embodiments, the periodic property includes a translational movement. In some embodiments, the translational movement is determined from accelerometer data. For example, the cyclic movement may exhibit an alternating between positive and negative acceleration, such as when the movement stops to change direction. Periodicity in this change of direction of acceleration corresponds to a cadence.

In some embodiments, the pitch, yaw, roll, or combination thereof is determined using an AHRS algorithm. In some embodiments, the determination of the cadence uses the same AHRS algorithm as the determination of posture. By doing so, computational load may be decreased as it reduces duplicative calculations. In some embodiments, the determination of the cadence includes reducing noise, drift or both.

In some embodiments, the activity is cycling. In cycling, cadence refers to the rate at which a user pedals the vehicle. Conventionally, cadence could be determined by sensors mounted on a vehicle (e.g. a bicycle), for example, a dyno connected to the vehicle's crank. However, such devices mounted to the vehicle itself may be difficult to install, remove, or transfer to another bicycle. As such, a head-worn device may simplify the set up and transfer of equipment. Alternatively, if the user had multiple vehicle-mounted devices, the costs may be increased compared to a single head-worn device. In cycling, it was discovered that the orientation head exhibited a rotation movement at about the same frequency as the pedaling motion. Other activities where cadence may be useful include rowing, running, or any other activity with a cyclic or periodic quality to the movement.

In some embodiments, pedaling rate in rotations per minute may be measured by head-worn movement sensors 112. For example, during pedaling movements, head orientation may rotate at the same frequency as the pedaling motion. Heading rotation may be found in all three axes of orientation (pitch, roll and yaw), and roll and yaw may be of particular interest.

Principal component analysis (PCA) may be used to find the main axis of head rotation in order to maximize the signal to noise ratio of the head rotation relating to cadence and applied to each moving window of windowed pitch, roll and yaw data.

The principal component (PC) of rotation may be found by two different methods: (i) finding the PC with highest periodicity in the frequency range of interest for each window, providing a changing PC vector across windows, and (ii) finding the mode of the PC with highest periodicity in the frequency range of interest across windows of a calibration set (for real-time processing) or the entire data array (for offline processing). The windowed data is then multiplied by the mode of the PC weights.

Conveniently, using the mode of the principal component may reduce errors from periodic head movements not associated with the cadence, for example a cyclist looking over his or her shoulder.

Cadence may also be measured with only one axis of orientation but may be less accurate if many other head movements unrelated to cadence are present in the data. Accelerometer data can be added to the processing to determine when the bike stops and set cadence to zero.

Figure 6:
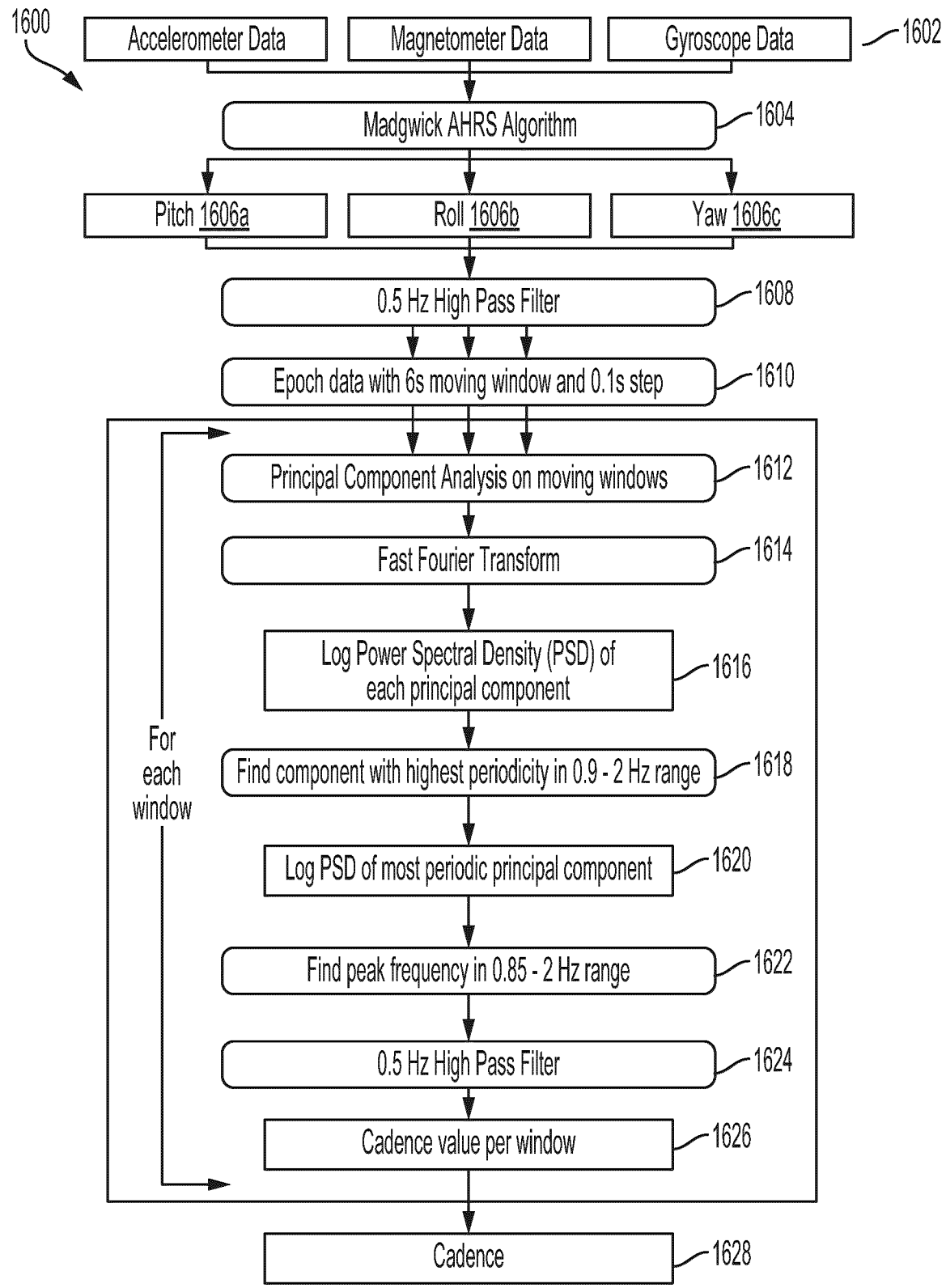
FIG. 6 illustrates a flow chart of a method for determining a cadence metric, performed by the software of FIG. 3, according to an embodiment.

FIG. 6 illustrates a flow chart of a method 1600 for determining a cadence metric, performed by cadence module 332 software of FIG. 3, according to an embodiment. The steps are provided for illustrative purposes. Variations of the steps, omission or substitution of various steps, or additional steps may be considered.

As shown in FIG. 6, sensor data 1602 may be received from movement sensor(s) 112. In particular, accelerometer data may be received from accelerometer 112*a*, magnetometer data may be received from magnetometer 112*c*, and gyroscope data may be received from gyroscope 112*b*.

Sensor data 1602 may then be processed at block 1604 using a Madgwick AHRS algorithm to determine a system state, in particular to determine pitch data 1606*a*, roll data 1606*b* and yaw data 1606*c*.

At block 1608, pitch data 1606*a*, roll data 1606*b* and yaw data 1606*c* may be filtered with a 0.5 Hz high pass filter.

At block 1610, specific time-windows are extracted from the filtered signal of each of pitch data 1606*a*, roll data 1606*b* and yaw data 1606*c* from block 1608, called "epochs", with a six second moving window and a 0.1 second step.

Blocks 1612 to 1626 are then performed for each window of pitch data, roll data, and yaw data windowed at block 1610.

At block 1612 principal component analysis (PCA) may be applied to each moving window to find the main axis of head rotation in order to maximize the signal to noise ratio of the head rotation relating to cadence.

At block 1614 a fast Fourier transform is applied to the data to generate and log a power spectral density (PSD) 1616 of each principal component.

At block 1618, the component with highest periodicity in 0.9-2 Hz range is found, and at log the PSD of the most periodic principal component 1620.

At block 1622, peak frequency in 0.85-2 Hz range is found, and passed through a 0.5 Hz high pass filter at block 1624, to determine a cadence value per window 1626, from which a cadence metric 1628 is determined.

In some embodiments, feedback on a cadence metric may be provided to a user in the form of a display. Having reference to FIG. 11, in an embodiment, an indicia of cadence 300 is shown. The indicia includes a cadence indicator 301. In some embodiments, the cadence indicator 301 includes a numerical cadence display 302. The numerical cadence display 302 is updated to show the frequency of the cadence. In some embodiments, the numerical cadence display 302 is updated at a rate of up to the polling rate of the movement sensors. In some embodiments, the numerical cadence display 302 is updated at a rate of up to about 52 Hz, preferably at a rate of from about 1 Hz to about 52 Hz. In some embodiments, the numerical cadence display 302 is updated at a rate of about 10 Hz. In some embodiments, the selection of the update rate is chosen to reduce computational load as compared to updating at every sample from the movement sensors (which may, for example, be polled at 52 Hz), while displaying small and fast changes in a smooth manner.

In some embodiments, at least a portion of the cadence indicator changes color according to the cadence. In some embodiments the at least a portion of the cadence indicator 301 is the numerical cadence display 302, or a stylized portion, or any combination thereof. In some embodiments, the at least a portion of the cadence indicator 301 is the numerical cadence display 302. In some embodiments, the color of the text, the color of the background behind the text, or both are changed on the numerical cadence display 302. In some embodiments, the text of the numerical cadence display 302 changes color according to the cadence. In some embodiments, the text color may correspond to the one or more cadence value or range of values. For example, as the user changes their cadence from a first value corresponding to a first cadence range to a second value corresponding to a second cadence range, the color of the text will change form a first color associated with the first cadence range to a second color associated with the second cadence range.

In some embodiments, the cadence indicator 301 includes a stylized portion 303. The stylized portion may be selected based on the activity. For example, when the activity is cycling, in some embodiments, the stylized portion 303 is a gear. In some embodiments, the stylized portion 303 is animated based on the cadence. For example, in some embodiments, the stylized portion 303 is a gear that rotates based on the cadence. In some embodiments, the gear is rotating at a frequency that is equal to the frequency of the cadence. In other embodiments, rotation is based on the rate of change of the frequency (i.e. the $1^{st}$ derivative of the frequency). For example, if the user maintains their cadence, the stylized portion will not rotate; as the user increases their cadence, the gear will rotate in a clockwise direction; and as the user decreases their cadence, the gear will rotate in a counter clockwise direction. In some embodiments, the cadence indicator includes a vertical or horizontal slider, or a live line graph. In some embodiments, cadence data may be displayed for the session, for example, on a graph.

Kinematics Metrics

In some embodiments, the at least one movement property includes a kinematic score. The kinematic score represents the efficiency and consistency of head movements during the activity. Whereas cadence measures the periodic movement of the head during an activity, the kinematic score reflects the consistency of the periodic movement. Thus, in some embodiments, if the user exhibits precisely the same movement for each period and the periodic movement is performed at the same rate, then the user would have a higher kinematic score than a user whose movement for the period exhibited deviations or whose periodic movements were performed at a different rate. In some embodiments, the kinematic score may provide by the user with feedback for adjusting their movements to improve the user's kinematics, or efficiency of movement.

In some embodiments, a kinematics metric may score the efficiency and consistency of head movements, for example, during biking, from head-worn movement sensor(s) 112. For example, a kinematic score may be higher for consistent movements and decreases as a result of a change in the movement pattern or due to inconsistent movements.

The main rotation axes considered for biking may be roll and yaw, for other applications any two axes of rotation could be used.

In some embodiments, a reference histogram, built with a 20 second window for a biking application, maps the pattern of movement in the two main axes of rotation. The shorter window, for example, three seconds for biking, is then used to compare the recent movements to the reference pattern. A reference window of 20 seconds may be used for the biking application to include sufficient cycles of cadence to differentiate between one consistent cadence pattern and shifting between two or more cadence patterns, for example, biking in a standing position followed by an aerodynamic racing position. A scoring window of three seconds was selected for the biking application as it represents approximately three cycles of cadence and therefore may represent efficiency across the most recent cycles of cadence. In other embodiments, a reference window and scoring window may be extended or shortened to other time lengths.

Figure 7:
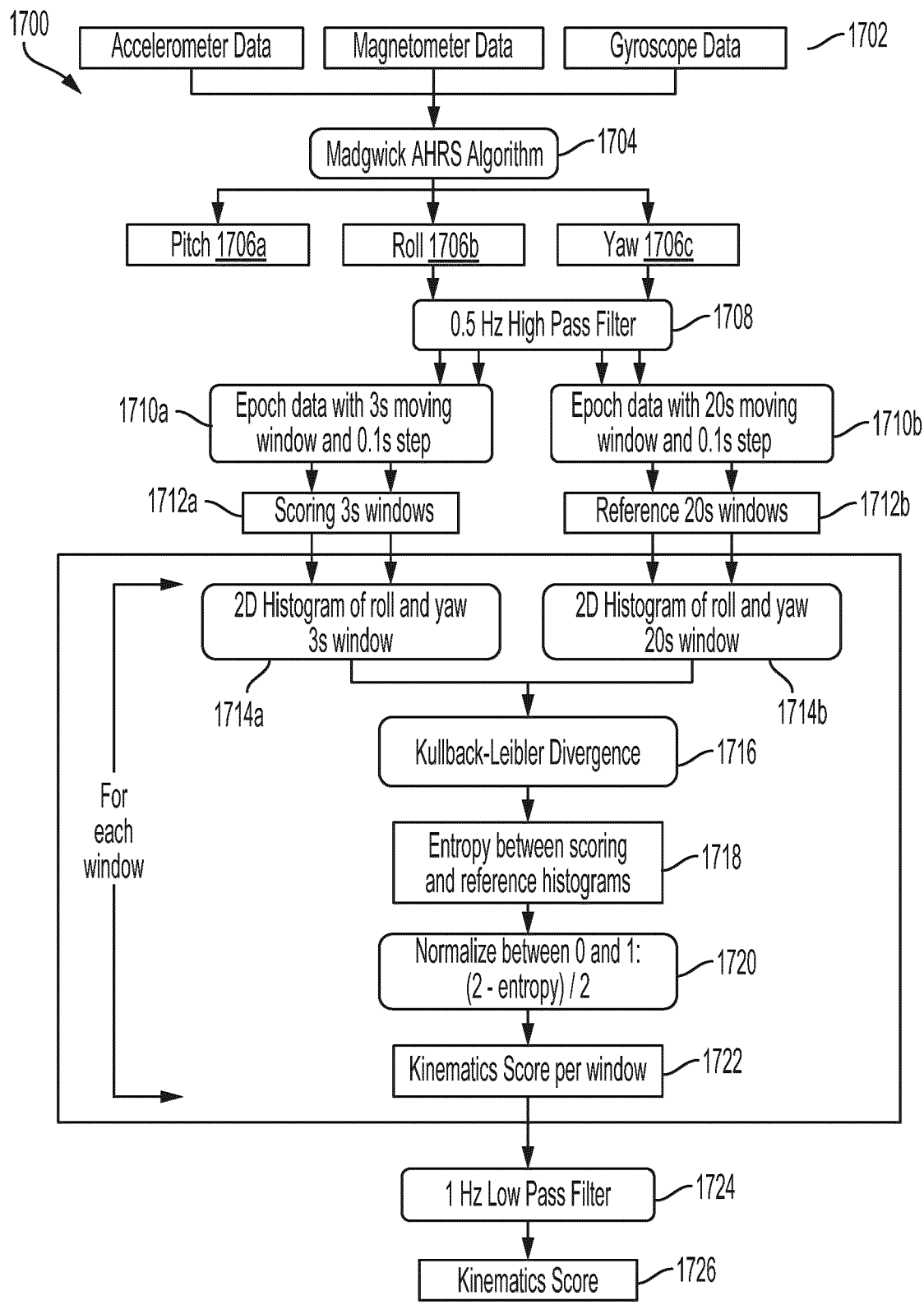
FIG. 7 illustrates a flow chart of a method for determining a kinematics metric, performed by the software of FIG. 3, according to an embodiment.

FIG. 7 illustrates a flow chart of a method 1700 for determining a kinematics metric, performed by kinematics module 333 software of FIG. 3, according to an embodiment. The steps are provided for illustrative purposes. Variations of the steps, omission or substitution of various steps, or additional steps may be considered.

As shown in FIG. 7, sensor data 1702 may be received from movement sensor(s) 112. In particular, accelerometer data may be received from accelerometer 112a, magnetometer data may be received from magnetometer 112c, and gyroscope data may be received from gyroscope 112b.

Sensor data 1702 may then be processed at block 1704 using a Madgwick AHRS algorithm to determine a system state, in particular to determine pitch data 1706a, roll data 1706b and yaw data 1706c.

Roll data 1706b and yaw data 1706c may be passed through a 0.5 Hz high pass filter at block 1708.

The filtered roll data 1706b and yaw data 1706c from block 1708 is then epoched to both a three second moving window and 0.1 second step at block 1710a to form scoring three second windows 1712a, and a 20 second moving window and 0.1 second step at block 1710b to form reference 20 second windows 1712b.

Blocks 1714a, 1714b to 1722 are then performed for each scoring and reference window of roll data, and yaw data windowed at blocks 1712a, 1712b.

At block 1714a, a 2D scoring histogram of roll and yaw from the three-second windows 1712a is generated. At block 1714b, a 2D reference histogram of roll and yaw from the twenty-second windows 1712b is generated.

At block 1716, Kullback-Leibler divergence is applied to the scoring histogram and the reference histogram to determine entropy 1718 between the scoring and reference histograms. At block 1720 this value is normalized between 0 and 1, to determine a kinematics score per window, from which a kinematics score 1726 is determined after passing through a 1 Hz low pass filter 1724.

In some embodiments, feedback on a kinematic metric may be provided to a user in the form of a display. Having reference to FIG. 11, in an embodiment, the display includes an indicia of kinematics 400. The indicia of kinematics 400 includes a kinematic score indicator 402. In some embodiments, the kinematic score indicator 402 includes a current score indicator 404. In some embodiments, the current score indicator includes a numerical indicator, a graphical marker, or both. In some embodiments, the kinematic score indicator 402 includes a historical score indicator 406. Similar to the current score indicator, in some embodiments, the historical score indicator 406 is a numerical indicator, a graphical indicator, or both.

In some embodiments, the kinematic score indicator 402 includes a scale indicator 408, and both the current score indicator 404 and the historical score indicator 406 are graphical indicators. In such embodiments, the current score indicator 404, the historical score indicator 406 and the scale indicator 408 together form a histogram. In the histogram, the current score indicator may be updated on the histogram at a graphical point. The scale indicator 406 can include a time axis and a kinematic score axis. In some embodiments, the current score indicator 404 moves along the time axis, the kinematic score axis, or both. In some embodiments, the upper and lower bounds of the time axis can be shifted to indicate kinematic score through passage of a period of time. In some embodiments where the bounds of the time axis are shifted, the current score indicator 404 moves along the time axis at the same rate that the upper and lower bounds are shifted, such that the position of the current score indicator 404 appears static with respect to its position along the time axis. In such embodiments, the current score indicator 404 appears to move only along the kinematic score axis. In some embodiments, as the upper and lower bounds of the time axis are shifted, the historical score indicator 406 is updated to show the kinematic score at the relevant time coordinate on the time axis.

Stillness Metrics

In some embodiments, the at least one movement property is balance (or stillness) metrics. In certain activities, a person needs to maintain a still position for certain periods of time. For example, the activity may be yoga. In yoga, a user moves through a series of position ("poses"), typically maintaining each pose for a period of time. Ideally, the user is perfectly still while maintaining a pose, appearing statuesque. However, when maintaining a pose, the user's limbs may be held in extended positions, or their weight may need to be balanced. Since the user's muscles are supporting the user's weight (e.g. a user's entire body weight, torso, limb, or combination thereof), the user's muscles experience strain during the period that the user maintains the pose. This strain on the muscles may cause the user to start shaking. In some embodiments, a "shake" is a movement exhibiting high frequency oscillations. Further, the user may not be positioned such that the weight is distributed properly, or the shaking causes greater disturbance in the user's position. This can cause the user to start "wobbling" or "sway". In some embodiments, a "wobble" is a movement exhibiting medium frequency oscillations. In some embodiments, such movements are exhibited when a user starts losing their balance. In some embodiments, a "sway" is a movement exhibiting low frequency oscillations. In some embodiments, such movements may be controlled or uncontrolled.

It was discovered that at least some of a user's shakes, wobbles, sways, or combinations thereof could be detected at movement sensors located at the head, even when such movements originated from muscle movements located elsewhere in the body. The frequency ranges for each movement type noted above were determined using synced video and movement sensor data taken during users' performances of yoga poses.

In some embodiments, the at least one movement sensor 112 includes an accelerometer, a gyroscope, a magnetometer, or combination thereof. Sensor data is analyzed to determine the amount of oscillations in the user's movement. In some embodiments, the amount of oscillations in the user's movement include a classification according to one or more movement frequency ranges. In some embodiments, the one or more movement frequency ranges includes a swaying movement range, a wobbling movement range, a shaking movement range, or combination thereof. In some embodiments, AHRS is optionally used to determine the oscillations in movement.

In some embodiments, the shaking movement range includes movement having a frequency of greater than about 5 Hz. In some embodiments, the frequency is from greater than about 5 Hz to about 25 Hz. In some embodiments, the wobbling movement range includes movement having a frequency of from about 2 Hz to about 5 Hz. In some embodiments, the swaying movement range includes movements having a frequency of less than about 2 Hz. In some embodiments, the swaying movement range has a frequency of between about 0.001 Hz and about 2 Hz. In some embodiments, the ranges do not overlap to reduce part of the same movement in two of the ranges.

Figure 8:
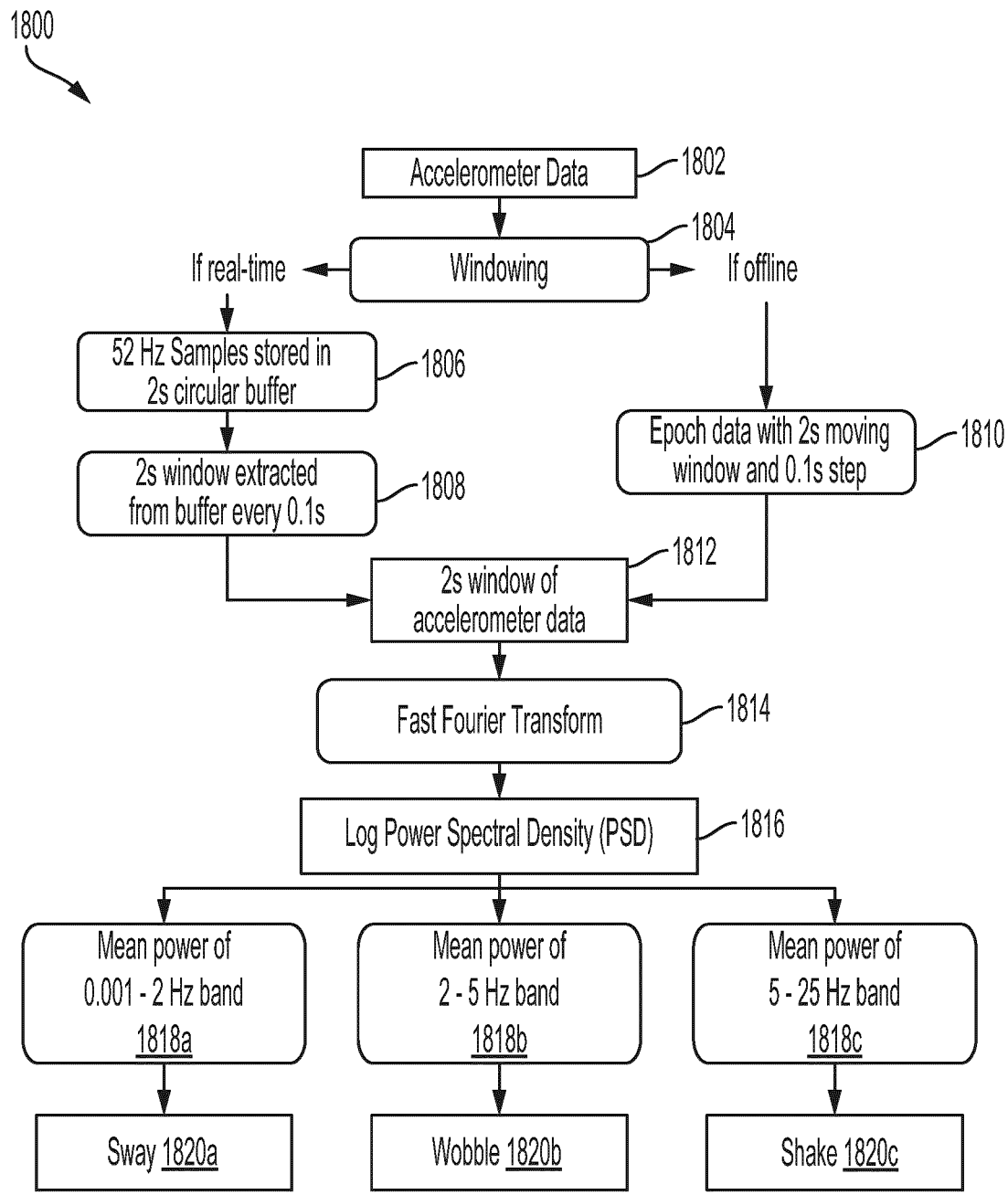
FIG. 8 illustrates a flow chart of a method for determining a stillness metric, performed by the software of FIG. 3, according to an embodiment.

FIG. 8 illustrates a flow chart of a method 1800 for determining a stillness metric, performed by stillness module 334 software of FIG. 3, according to an embodiment. The steps are provided for illustrative purposes. Variations of the steps, omission or substitution of various steps, or additional steps may be considered.

As shown in FIG. 8, sensor data 1802 may be received from movement sensor(s) 112. In particular, accelerometer data may be received from accelerometer 112a. In some embodiments, other sensor data such as magnetometer data may be received from magnetometer 112c, and gyroscope data may be received from gyroscope 112b.

Sensor data 1802 may then be windowed at block 1804.

If sensor data is being processed in real-time, control flow continues to block 1806, at which 52 Hz samples are stored in two-second circular buffer. At block 1808, a two-second window is extracted from the buffer every 0.1 seconds, resulting in two-second window of accelerometer data 1812.

If sensor data is being processed offline, control flow continues from block 1804 to block 1810 to epoch the data with a two-second moving window and a 0.1 second step, resulting in two-second window of accelerometer 1812.

At block 1814, a fast Fourier transform is applied, and the power spectral density (PSD) logged at block 1816.

The mean power of the 0.001-2 Hz frequency band is calculated to determine a sway metric 1820a. The mean power of the 2-5 Hz frequency band is calculated to determine a wobble metric 1820b. The mean power of the 5-25 Hz frequency band is calculated to determine a shake metric 1820c.

In some embodiments, feedback on a stillness metric may be provided to a user in the form of a display. Having reference to FIG. 12, in an embodiment, the display 130 includes an indicia of stillness 600. In some embodiments, the indicia 600 includes at least one movement indicator or stillness indicator 610 for indicating a user's movement.

In some embodiments, each of the at least one movement indicator 610 independently indicates the amount of movement in a respective movement frequency range. For example, in some embodiments, the at least one movement indicator 610 includes a shake indicator 610a, a wobble indicator 610b, and a sway indicator 610c. In some embodiments, the at least one movement indicator 610 is modified to show the change in the movement frequency range associated with that movement indicator. For example, in some embodiments, at least one of the at least one movement indicator is a circle. The circle may be sized (e.g. expanded or contracted), moved (e.g. toward or away from a focal position), or both, depending on the amount of movement in the particular movement frequency range.

In some embodiments, the at least one movement indicator 610 includes a plurality of movement indicators 610. In some embodiments, when no movement is detected any of the movement frequency ranges associated with the plurality of movement indicators, the plurality of movement indicators converge to a common size, position, or both. For example, the indicators may converge on the focal position with a convergence size such that a viewer at the display would see a single movement indicator. As the user exhibits movements of a particular movement frequency, the movement indicator having a movement frequency range associated with the particular movement frequency is moved, sized, or both, according to the movement. This would disrupt the convergence of the movement indicators and provide feedback to the user that they are not still, and the type of motion that they are exhibiting. The display may provide feedback to the user in the form of a visual objective that they may try to obtain while performing yoga poses, providing gamification of the stillness of a pose. In some embodiments, feedback may be provided to the user in the form of auditory feedback, for example, corresponding to different sounds or tones of different frequency for each movement frequency range, or tactile feedback by way of effectors, for example, on head-worn device 110.

In some embodiments, the indicia 600 includes a legend 604 differentiating the type of movement associated with each of the at least one movement indicators 610.

Focus Metrics

In some embodiments, the movement property includes focus metrics. The focus determination may be based on the activity being undertaken.

In some embodiments, focus is based on movement of the user's eyes. For example, during yoga, a pose is typically associated with a particular "drishti" (Sanskrit for focused gaze). In some embodiments, drishti includes a position or direction at which the user's gaze should be directed. Thus when a user is holding a pose, the user maintains drishti by focusing their gaze at a fixation position, ideally, without their gaze deviating therefrom. Deviations indicate that the user has not achieved a focused gaze.

In some embodiments, focus is based on the brain state of the user. For example, focus may be based on whether the user enters a meditative state, during which a user's brain waves would exhibit changes in specific band powers.

In some embodiments, the focus includes a focus score based on eye movements, brain states, or a combination thereof.

In some embodiments, the at least one movement sensor 112 includes at least one electrophysiological sensor.

In some embodiments, the at least one electrophysiological sensor includes at least one electroencephalogram (EEG) sensor. Brain state data may be determined from the at least one EEG sensor. In some embodiments, the focus score is based on the brain state. In some embodiments, the focus score may be based at least in part on brain event activity.

In some embodiments, the at least one electrophysiological sensor includes at least one eye movement sensor. In some embodiments, the at least one eye movement sensor includes an electrooculogram (EOG) sensor, an optical tracking sensor, an eye-attached sensor, or any combination thereof. In some embodiments, the at least one eye movement sensor includes an EOG sensor. The EOG sensor may be relatively lighter, consume less power, work in low light conditions, and be less expensive than an optical tracker. Similarly, the EOG sensor may be easier to use and cheaper than an eye-attached sensor, such a sensor embedded in a contact lens. However, the EOG may be less accurate at determining an absolute position of a user's gaze. Rather, the EOG sensor tends to indicate changes in the user's gaze. Thus, in some embodiments, the at least one eye movement sensor includes some combination of EOG sensor, optical tracking sensor, and eye-attached sensor to maximize the utility of the eye movement sensor.

In some embodiments, sensor data from the at least one eye movement sensor is used to determine the amount of eye movement. In some embodiments, the focus score is based on the amount of eye movement. In some embodiments, the focus score is inversely correlated with the amount of eye movement.

In some embodiments, feedback on a focus metric may be provided to a user in the form of a display. Having reference to FIG. 12, in an embodiment, the display 130 includes an indicia of focus 700. In some embodiments, the indicia of focus 700 includes a focus score indicator 702. In some embodiments, the focus score indicator 702 includes a current score indicator 704. In some embodiments, the current score indicator includes a numerical indicator, a graphical marker, or both. In some embodiments, the focus score indicator 702 includes a historical score indicator 706. Similar to the current score indicator, in some embodiments, the historical score indicator 706 is a numerical indicator, a graphical indicator, or both.

In some embodiments, the focus score indicator 702 includes a scale indicator 708, and both the current score indicator 704 and the historical score indicator 706 are graphical indicators. In such embodiments, the current score indicator 704, the historical score indicator 706 and the scale indicator 708 together form a histogram. In the histogram, the current score indicator may be updated on the histogram at a graphical point. The scale indicator 706 can include a time axis and a focus score axis. In some embodiments, the current score indicator 704 moves along the time axis, the focus score axis, or both. In some embodiments, the upper and lower bounds of the time axis can be shifted to indicate focus score through passage of a period of time. In some embodiments where the bounds of the time axis are shifted, the current score indicator 704 moves along the time axis at the same rate that the upper and lower bounds are shifted, such that the position of the current score indicator 704 appears static with respect to its position along the time axis. In such embodiments, the current score indicator 704 appears to move only along the focus score axis. In some embodiments, as the upper and lower bounds of the time axis are shifted, the historical score indicator 706 is updated to show the focus score at the relevant time coordinate on the time axis.

In some embodiments the indicia 700 includes one or more focus score range indicators 710. In some embodiments, the one or more focus score range indicators 710 include a focused range indicator 710a, a neutral range indicator 710b, and an unfocused range indicator 710c. In some embodiments, the one or more focus score range indicators 708 are associated with focus scores in particular ranges. In some embodiments, the focus score varies on a continuum from 0 to 1. In some embodiments, ranges divide the continuum evenly. For example, an unfocused range may be from 0 to ⅓, the neutral range may be from above ⅓ to ⅔, the focused range may be from above ⅔ to 1. Other distributions of focus score ranges and the number of ranges may be possible.

Ballistocardiogram Metrics

In some embodiments, the movement property includes ballistocardiographic metrics such as heart rate and heartbeat. The heart rate of a user may be determined from a head-worn movement sensor(s) 112, and based on the activity being undertaken.

Figure 9:
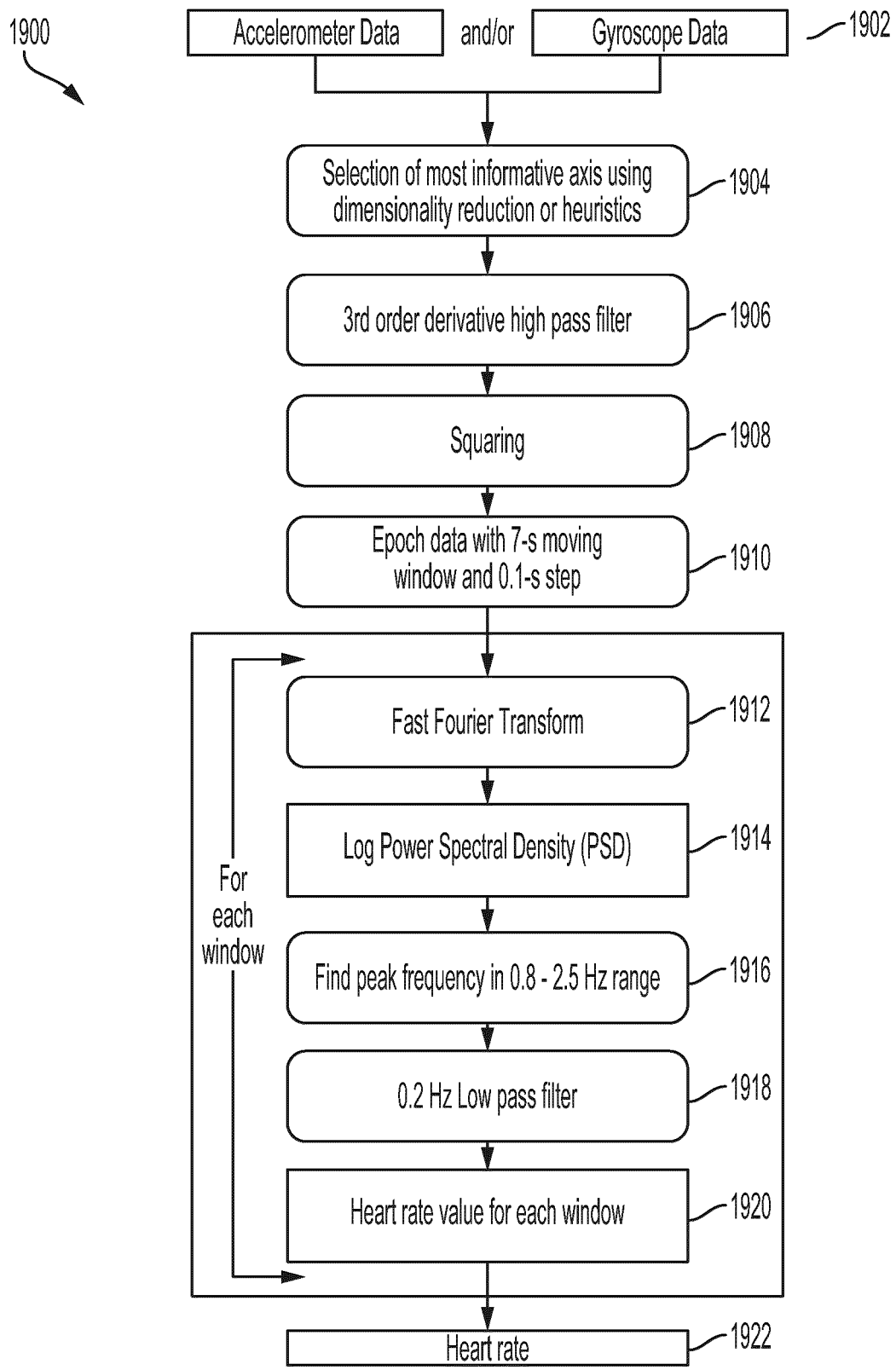
FIG. 9 illustrates a flow chart of a method for determining a heart rate metric, performed by the software of FIG. 3, according to an embodiment.

FIG. 9 illustrates a flow chart of a method 1900 for determining a heart rate metric, performed by ballistocardiogram module 336 software of FIG. 3, according to an embodiment. The steps are provided for illustrative purposes. Variations of the steps, omission or substitution of various steps, or additional steps may be considered.

As shown in FIG. 9, sensor data 1902 may be received from movement sensor(s) 112. In particular, accelerometer data may be received from accelerometer 112*a*, and/or gyroscope data may be received from gyroscope 112*b*.

At block 1904, selection of the most informative axis is performed using dimensionality reduction or heuristics.

At block 1906, third order derivative high pass filtering is applied.

At block 1908, squaring is applied.

At block 1910, the data is epoched into windows with seven-second moving window and a 0.1 second step.

Blocks 1912 to 1920 are then performed for each window of accelerometer data and/or gyroscope data windowed at block 1910.

At block 1912, a fast Fourier transform is performed, and the power spectral density (PSD) 1914 logged.

At block 1916, peak frequency in the 0.8-2.5 Hz range is found, and passed through a 0.2 Hz low pass filter at block 1918, to determine a heart rate value for each window 1920, to determine a heart rate metric 1922.

Figure 10:
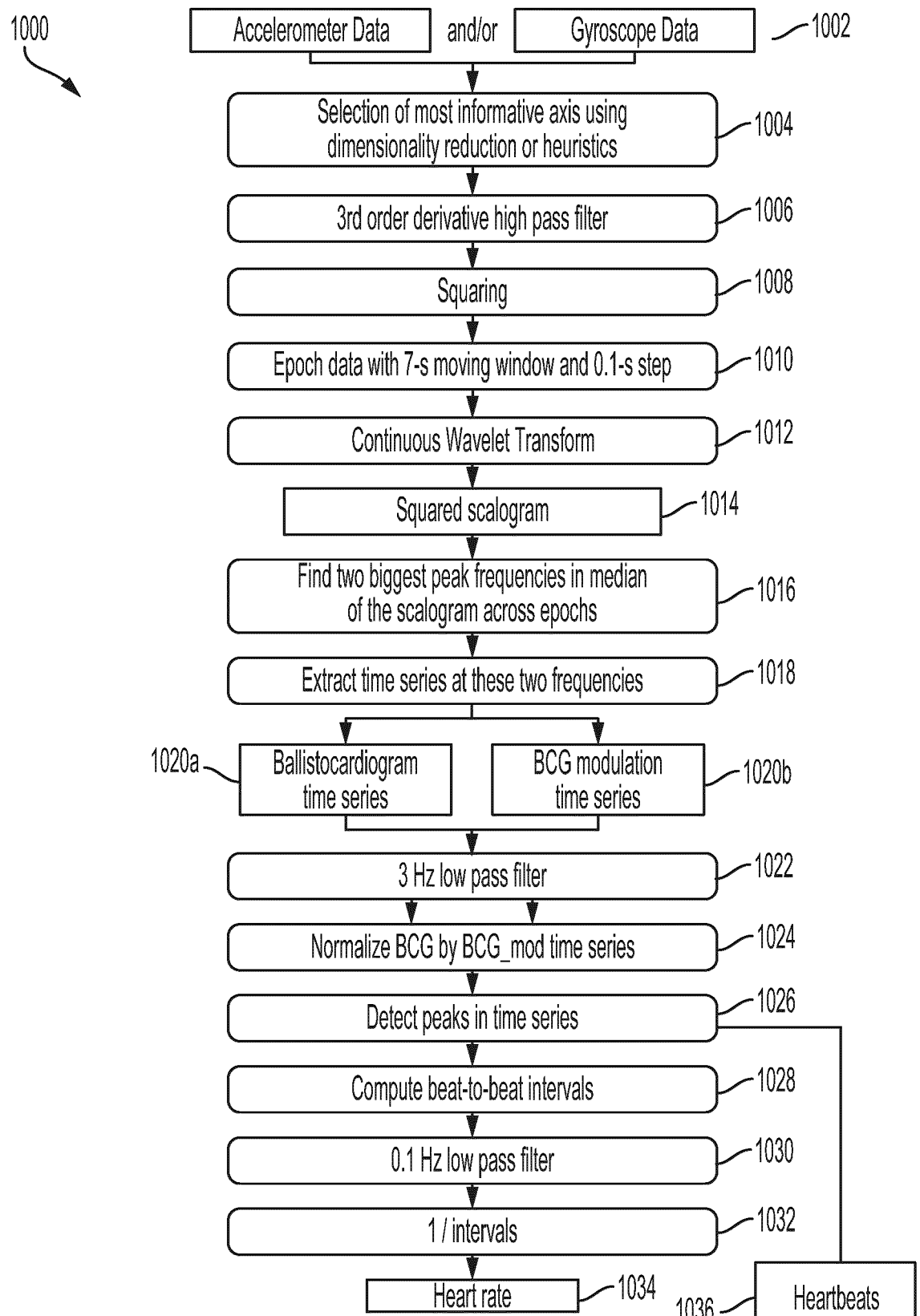
FIG. 10 illustrates a flow chart of a method for determining a heart rate metrics and a heartbeat metric, performed by the software of FIG. 3, according to an embodiment.

FIG. 10 illustrates a flow chart of a method 1000 for determining a heart rate metric and a heartbeat metric, based on a wavelet transform, performed by ballistocardiogram module 336 software of FIG. 3, according to an embodiment. The steps are provided for illustrative purposes. Variations of the steps, omission or substitution of various steps, or additional steps may be considered.

As shown in FIG. 10, sensor data 1002 may be received from movement sensor(s) 112. In particular, accelerometer data may be received from accelerometer 112*a*, and/or gyroscope data may be received from gyroscope 112*b*.

At block 1004, selection of the most informative axis is performed using dimensionality reduction or heuristics.

At block 1006, third order derivative high pass filtering is applied.

At block 1008, squaring is applied.

At block 1010, the data is epoched into windows with seven-second moving window and a 0.1 second step.

At block 1012, a continuous wavelet transform is applied to generate a squared scalogram 1014.

At block 1016, the two biggest peak frequencies in median of the scalaogram is found across epochs.

At block 1018, time series is extracted at these two frequencies, resulting in a ballistocradiogram time series 1020*a* and a ballistocardiogram (BCG) modulation time series 1020*b*, each of which is passed through a 3 Hz low pass filter at block 1022.

At block 1024, the ballistocardiogram is normalized by the filtered BCG modulation time series.

At block 1026, peaks are detected in the time series, identifying heartbeats metric 1036.

At block 1028, beat-to-beat intervals are computed and passed through a 0.1 Hz low pass filter at block 1030, which are then inverted at block 1032 to result in a heart rate metric 1034.

In some embodiments, feedback on a ballistocardiogram metric such as a heart rate metric or a heartbeat metric may be provided to a user in the form of a display or other feedback such as audio, in an example, an audio sound to match the determined heart rate or heartbeat of the user. A user may, for example, attempt to synchronize their movement to heart rate or breathing rate.

General

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances, without departing from the scope of the invention, which is to be limited only by the claims.

What is claimed is:

1. A wearable system for determining at least one movement property comprising:
   a head-mountable device including at least one movement sensor for sensing movement of a head of a user;
   a processor in communication with the at least one movement sensor;
   a feedback module in communication with the processor; and
   a memory in communication with said processor, said memory storing instructions thereon that when executed cause the processor to:
      obtain sensor data from the at least one movement sensor;
      determine at least one first movement type relating to movement based at least in part on a first frequency range of the sensor data obtained from the at least one movement sensor and at least one second movement type relating to movement based at least in part on a second frequency range of the sensor data, wherein the movement relates to one or more body parts of the user located elsewhere from the head of the user, wherein the first and the second frequency ranges include at least two of:
- a high frequency range indicative of a shaking movement type;
- a medium frequency range indicative of a wobbling movement type; and
- a low frequency range indicative of a swaying movement type; and determine a stillness metric based on the first and second movement types;

generate real-time feedback for a user relating to each of the first and second movement types using the feedback module, wherein the real-time feedback is at least one of visual, auditory and tactile, wherein the real-time feedback is based on a target stillness metric and the determined stillness metric.

2. The system of claim 1, wherein the low frequency range has a frequency of less than about 2 Hz, the medium frequency range has a frequency of between about 2 Hz and about 5 Hz, and the high frequency range has a frequency of greater than about 5 Hz.

3. The system of claim 1, wherein the at least one first or the at least one second movement type is determined based at least in part on mean power of the frequency ranges.

4. The system of claim 1, wherein the memory stores instructions thereon that when executed cause the processor to determine a periodic frequency of the sensor data, the at least one first or the at least one second movement type property is determined based at least in part on the periodic frequency, and the real-time feedback for a user relating to each of the at least one first or the at least one second movement type includes a numerical indicator showing the periodic frequency.

5. The system of claim 4, wherein the periodic frequency is determined based at least in part on movement detected along at least one axis of rotation chosen from a pitch, a yaw, a roll, or a combination thereof.

6. The system of claim 1, wherein the memory stores instructions thereon that when executed cause the processor to:
- calibrate the sensor data to a frame of reference;
- determine a target metric within the frame of reference;
- compare the at least one first or the at least one second movement type to the target metric; and
- display a representation of the comparison on the display.

7. The system of claim 6, wherein parameters of the frame of reference are determined on the basis of at least one of previous data for a user, a population norm, and an external reference.

8. The system of claim 6, wherein the representation of the comparison is offset by a pre-determined value.

9. The system of claim 1, wherein the at least one movement sensor comprises an electrophysiological sensor, a gyroscope, an accelerometer, a magnetometer, a camera or combination thereof.

10. The system of claim 1, wherein the determining of the at least one first and second movement types comprises obtaining a pitch, a yaw, a roll, or combination thereof based on the sensor data obtained from the at least one movement sensor using an attitude and height reference.

11. The system of claim 1, wherein the at least one first and second movement types is determined based at least in part on a brain state and an eye movement, and the real-time feedback for a user relating to each of the at least one first or the at least one second movement type includes a scale indicator including a time axis and a focus score axis and a focus score indicator showing a user's focus score on the scale indicator.

12. The system of claim 11, wherein the focus score indicator comprises a current score indicator for showing the user's current focus score on the scale indicator; and a historical score indicator showing the user's previous focus scores on the scale indicator.

13. The system of claim 1, wherein the at least one first or the at least one second movement type is determined based at least in part on a pitch and a position determined from the sensor data, and the indicia of the at least one first or the at least one second movement type includes a posture scale indicating a possible range of posture values and a posture marker indicating the user's current posture relative to the posture scale.

14. The system of claim 13, wherein the real-time feedback for a user relating to each of the at least one first or the at least one second movement type comprises:
- a reference frame for showing a range of possible positions; and
- a current position indicator overlaid on top of the reference frame for displaying a current position of the user.

15. The system of claim 13, wherein the real-time feedback for a user relating to each of the at least one first or the at least one second movement type comprises a desired position indicator showing a desired range of positions for a pose of the user.

16. The system of claim 13, wherein the real-time feedback for a user relating to each of the at least one first or the at least one second movement type comprises a previous position range indicator.

17. The system of claim 1, wherein the at least one first or the at least one second movement type is determined based at least part on the sensor data from a scoring window of time as compared to the sensor data from a reference window of time, and the real-time feedback for a user relating to each of the at least one first and second movement types includes a scale indicator including a time axis and a kinematic score axis and a kinematic score indicator showing the user's kinematic score on the scale indicator.

18. The system of claim 17, wherein the kinematic score indicator comprises a current score indicator for showing the user's current kinematic score on the scale indicator; and a historical score indicator showing the user's previous kinematic scores on the scale indicator.

* * * * *